United States Patent
Ebsen et al.

(10) Patent No.: US 9,228,982 B2
(45) Date of Patent: Jan. 5, 2016

(54) SINGLE INJECTION VALVE FOR HPLC COMBINING SAMPLE INTRODUCTION, WASH CYCLES AND DIAGNOSIS

(75) Inventors: Johnny Ebsen, Pfinztal (DE); Matthias Wetzel, Landau (DE)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 712 days.

(21) Appl. No.: 13/235,083

(22) Filed: Sep. 16, 2011

(65) Prior Publication Data
US 2013/0067997 A1  Mar. 21, 2013

(51) Int. Cl.
*G01N 30/20* (2006.01)
*G01N 30/24* (2006.01)

(52) U.S. Cl.
CPC ............. *G01N 30/20* (2013.01); *G01N 30/24* (2013.01); *G01N 2030/202* (2013.01); *G01N 2030/207* (2013.01)

(58) Field of Classification Search
CPC ............ G01N 30/20; G01N 2030/207; G01N 2030/202; G01N 30/24
USPC .............. 210/635, 656, 659, 101, 143, 198.2; 422/70
See application file for complete search history.

(56) References Cited

U.S. PATENT DOCUMENTS

| | | | |
|---|---|---|---|
| 4,068,528 A | 1/1978 | Gundelfinger | |
| 4,923,167 A | 5/1990 | Schmidt | |
| 6,155,123 A | 12/2000 | Bakalyar | |
| 6,942,793 B2* | 9/2005 | Ito et al. | 210/198.2 |
| 8,048,312 B2* | 11/2011 | Deguchi et al. | 210/656 |
| 2002/0011437 A1* | 1/2002 | Kaito et al. | 210/198.2 |
| 2003/0042189 A1* | 3/2003 | Shirota et al. | 210/198.2 |
| 2003/0098076 A1 | 5/2003 | Nichols | |
| 2003/0168392 A1* | 9/2003 | Masuda et al. | 210/198.2 |
| 2004/0173509 A1* | 9/2004 | Ito et al. | 210/94 |
| 2004/0178133 A1* | 9/2004 | Deguchi et al. | 210/198.2 |
| 2010/0101989 A1* | 4/2010 | Berndt | 210/188 |
| 2012/0132013 A1* | 5/2012 | Glatz et al. | 73/863.02 |
| 2012/0305464 A1* | 12/2012 | Cormier | 210/198.2 |

FOREIGN PATENT DOCUMENTS

| | | |
|---|---|---|
| EP | 309596 | 4/1989 |
| EP | 0321774 A2 | 6/1989 |
| EP | 1577012 A1 | 9/2005 |

\* cited by examiner

*Primary Examiner* — Ernest G Therkorn

(57) ABSTRACT

A switchable valve for a sample injector includes a first valve member and a second valve member that can moved with respect to the other. The first valve member includes a plurality of ports, the second valve member includes a plurality of fluid paths. The plurality of ports include eight circumferential ports distributed along a circumference and one central port arranged at a central position of the first valve member. The plurality of fluid paths include three arcuate fluid paths so as to be couplable with at least two of the circumferential ports and one straight fluid path extending between the central position and a circumferential position so as to be couplable with the central port and one of the circumferential ports.

11 Claims, 14 Drawing Sheets

# SINGLE INJECTION VALVE FOR HPLC COMBINING SAMPLE INTRODUCTION, WASH CYCLES AND DIAGNOSIS

BACKGROUND ART

The present invention relates to switchable valves, particularly for sample injectors, more particularly for a high performance liquid chromatography application.

In high performance liquid chromatography (HPLC, see for instance http://en.wikipedia.org/wiki/HPLC), a liquid has to be provided usually at a very controlled flow rate (e.g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid.

Valves are commonly used in HPLC applications, for instance injection valves for introducing a liquid sample into a high pressure flowing stream of liquid, purge valves for positive displacement pumps, flow path switching valves, etc. Such valves used in HPLC applications are often multi-position rotary valves. Examples of multi-position rotary valves are disclosed in U.S. Pat. No. 4,068,528 A (two-position valves) or US 2003/0098076 A1 (multi-function rotary valves or random-access, dual, three-way, rotary switching valves).

Shear valves, which can be used in multi-way embodiments, are usually formed by a housing and a body defining a stepped cavity in which the rotor or seal is positioned. The housing contains at least two shear seal valve members positioned to be aligned with ports in the rotor (body) to establish communication between the shear seal means. Shear valves are usually provided as rotary valves (such as the aforementioned rotary valves) or translational valves (often also called sliding valves), such as disclosed in EP 0321774 A2.

A multi-way switching valve provides a means for selectively routing a fluid input flow to the valve to one of more alternate output flows from the valve. A rotary valve is of the type wherein fluid flow is directed by rotating a valve rotor element to discrete angular positions relative to a stationary valve stator element. A dual rotary valve provides two valves in one valve body, both simultaneously operated by the positioning of the valve rotor. Rotary switching valves are commonly used, for example, in HPLC and other analytical methods to selectively direct a flow stream of one or more fluids along alternate paths to an analytical device or containment vessel.

U.S. Pat. No. 6,155,123 discloses a sample inject valve system, which enables a modified sample injection valve to perform many functions that are required to inject a sample into a chromatographic column, to minimize the amount of laboratory table space previously occupied by equipment and to organize and minimize the number of tubular fluid connections. The modified valve includes a stator with twelve passages lying on a circle centered on a rotor axis and a rotor with four channels for connecting selected passages. The stator passages are spaced 30° apart to lie at the twelve positions of a clock face. Each rotor channel has channel ends spaced by 30° and with the ends of different but adjacent channels spaced apart by 60°. Not only are the usual column, pump, sample loop ends, and metering syringe connected to stator passages, but a rinse syringe, rinse reservoir, waste syringe and a rinse nozzle are connected to other stator passages. The rotor has a radially-extending channel part with its outer end lying halfway between first and second channel and with its inner end lying at the rotor axis and connecting to a stator passage part that extends along the axis, to couple the pump to a third passage at all rotor positions.

In modern sample injectors, many functions need to be supported by a switchable valve. Conventional switchable valves may be inappropriate for such multi-function applications.

DISCLOSURE

It is an object of the invention to provide a switchable valve capable of supporting multiple functions in a sample injector. The object is solved by the independent claims. Further embodiments are shown by the dependent claims.

According to an embodiment of a first aspect of the present invention, a switchable valve for a sample injector for use in a fluid separation system for separating compounds of a sample fluid in a mobile phase is provided, the switchable valve comprising a first valve member and a second valve member, wherein at least one of the first and second valve members is configured to be moved with respect to the other, the first valve member comprises a plurality of ports (wherein each port may be fluidically connectable to a respective fluidic member), the second valve members comprises a plurality of fluid paths for fluidly coupling respective ones of the ports in dependency on a relative movement position of the first and second valve members with respect to each other, wherein the plurality of ports comprise eight (particularly exactly eight) circumferential ports distributed along a circumference of the first valve member and comprise one central port arranged at a central position of the first valve member, wherein one of the circumferential ports has an extension groove (wherein the extension groove may extend in or along a surface plane of the first valve member, and wherein the port in direct fluid communication with the extension groove may extend perpendicular to the surface plane of the first valve member), wherein the plurality of fluid paths comprise three (particularly exactly three) arcuate (or bent or curved) fluid paths each being arcuate so as to be couplable with at least two of the circumferential ports, wherein the plurality of fluid paths comprise one (particularly exactly one) straight fluid path extending between the central position and a circumferential position so as to be couplable with the central port and with one of the circumferential ports.

According to another embodiment of the first aspect of the present invention, a sample injector configured to introduce a sample fluid into a mobile phase is provided, wherein the mobile phase is to be driven by a mobile phase drive through a separation unit for separating compounds of the sample fluid in the mobile phase, the sample injector comprising a sample loop for receiving the sample fluid, and a switchable valve having the above mentioned features for switching the sample loop between the mobile phase drive and the separation unit.

According to another embodiment of the first aspect of the present invention, a fluid separation system for separating compounds of a sample fluid in a mobile phase is provided, the fluid separation system comprising a mobile phase drive, particularly a pumping system, configured to drive the mobile phase through the fluid separation system, a separation unit, particularly a chromatographic column, configured for separating compounds of the sample fluid in the mobile phase, and a switchable valve having the above mentioned features being operable for introducing the sample fluid into the mobile phase being conducted between the mobile phase drive and the separation unit.

According to still another embodiment of the first aspect of the present invention, a method of operating a switchable valve having the above mentioned features for a sample injector for use in a fluid separation system for separating compounds of a sample fluid in a mobile phase is provided, wherein the method comprises moving the first valve member and the second valve member with respect to one another for fluidically coupling respective ones of the ports in dependency on a relative movement position of the first and second valve members with respect to each other.

According to an embodiment of a second aspect of the present invention, a sample injector for use in a fluid separation system for separating compounds of a sample fluid in a mobile phase is provided, the fluid separation system comprising a mobile phase drive to drive the mobile phase and comprising a separation unit for separating compounds of the sample fluid in the mobile phase, the sample injector comprising exactly one switchable valve, a sample loop in fluid communication with a port of the valve and configured for receiving the sample fluid, a needle in fluid communication with the sample loop, a seat for receiving the needle, and a seat capillary in fluid communication with the seat and a port of the valve, wherein the valve is configured to be switchable so as to activate at least one selected of the following operation modes: a) a bypass mode in which the valve fluidically couples the mobile phase drive with the separation unit via the valve, b) a flush mode in which the valve enables flushing of at least one of the group consisting of the needle and the seat, and c) a block mode in which the valve fluidically couples at least the sample loop, the needle, the seat and the seat capillary to one another and fluidically decouples at least the sample loop, the needle, the seat and the seat capillary from the mobile phase drive, from the separation unit and from ambient pressure.

According to still another embodiment of the second aspect of the present invention, a method of operating a sample injector for use in a fluid separation system for separating compounds of a sample fluid in a mobile phase is provided, the fluid separation system comprising a mobile phase drive to drive the mobile phase and comprising a separation unit for separating compounds of the sample fluid in the mobile phase, the sample injector comprising exactly one switchable valve, a sample loop in fluid communication with a port of the valve and configured for receiving the sample fluid; a needle in fluid communication with the sample loop, a seat for receiving the needle, and a seat capillary in fluid communication with the seat and a port of the valve, wherein the method comprises switching the valve for selectively (i.e. a user or a control unit may select which of the procedures is carried out, the system having the capability of carrying out any one of these procedures) performing at least one of the following procedures: a) fluidically coupling the mobile phase drive with the separation unit via the valve; b) flushing at least one of the group consisting of the needle and the seat, c) fluidically coupling at least the sample loop, the needle, the seat and the seat capillary to one another and (particularly simultaneously) fluidically decoupling at least the sample loop, the needle, the seat and the seat capillary from the mobile phase drive, from the separation unit and from ambient pressure.

According to an embodiment of a third aspect of the present invention, a sample injector for use in a fluid separation system for separating compounds of a sample fluid in a mobile phase is provided, the fluid separation system comprising a mobile phase drive to drive the mobile phase and comprising a separation unit for separating compounds of the sample fluid in the mobile phase, the sample injector comprising exactly one switchable valve, a sample loop in fluid communication with a port of the valve and configured for receiving the sample fluid, a needle in fluid communication with the sample loop, a seat for receiving the needle, a seat capillary in fluid communication with the seat and a port of the valve, exactly one flush pump in fluid communication with a port of the valve and configured for flushing of at least one of the group consisting of the needle and the seat, and a wash port in fluid communication with a port of the valve, wherein the valve is configured to be switchable so as to activate at least one selected of the following operation modes: a) a sample path flush mode in which at least the sample loop and the needle (optionally also the seat and the seat capillary) are flushed by the flush pump; b) a seat back flush mode in which the seat is back flushed by the flush pump; and c) a needle wash mode in which the needle is washed in the wash port.

According to still another embodiment of the third aspect of the present invention, a method of operating a sample injector for use in a fluid separation system for separating compounds of a sample fluid in a mobile phase is provided, the fluid separation system comprising a mobile phase drive to drive the mobile phase and comprising a separation unit for separating compounds of the sample fluid in the mobile phase, the sample injector comprising exactly one switchable valve, a sample loop in fluid communication with a port of the valve and configured for receiving the sample fluid, a needle in fluid communication with the sample loop, a seat for receiving the needle, a seat capillary in fluid communication with the seat and a port of the valve, exactly one flush pump in fluid communication with a port of the valve and configured for flushing of at least one of the group consisting of the needle and the seat, and a wash port in fluid communication with a port of the valve, wherein the method comprises switching the valve for selectively (i.e. a user or a control unit may select which of the procedures is carried out, the system having the capability of carrying out any one of these procedures) performing at least one of the following procedures: a) flushing at least the sample loop and the needle (optionally also the seat and the seat capillary) by the flush pump, b) back flushing the seat by the flush pump, and c) washing the needle in the wash port.

According to still another embodiment of the present invention, a fluid separation system for separating compounds of a sample fluid in a mobile phase is provided, the fluid separation system comprising a mobile phase drive, particularly a pumping system, configured to drive the mobile phase through the fluid separation system, a separation unit, particularly a chromatographic column, configured for separating compounds of the sample fluid in the mobile phase, and any of the above described sample injectors (i.e. of the first, second or third aspect).

According to the first aspect of the invention, a powerful fluidic valve is provided made of two valve members such as a rotor and a stator being movable, particularly rotatable, with respect to one another so as to bring individual ones of the ports (connectable to various fluidic components of the sample injector) in alignment with certain fluidic paths such as grooves. In other words, by moving the two valve members relative to one another, a plurality of different operation modes can be adjusted which are to be carried out within the context of a sample separation procedure, particularly a liquid chromatography procedure. By positioning at least eight circumferential ports along a perimeter of the first valve member, and by extending one fluidic port thereof by an extension groove formed in a surface portion of the first valve member, a structure is provided which properly cooperates with the second valve member having at least three arcuate fluid paths for fluid communication to the circumferential ports, and having one fluid path extending radially along the second valve member for fluid communication with the central port. This combination of ports and fluid paths in the cooperating valve members allows obtaining an injection valve which can be used as a single injection valve for an HPLC sample injector combining tasks such as sample injection, wash cycles and diagnosis. Therefore, a highly compact sample injector may be constructed based on such a fluidic device. Furthermore, the number of seals can be reduced to a very small value when implementing only one valve in the sample injector, so that leakage due to improper sealing becomes less of an issue. Moreover, operation of a single valve is significantly easier for a user than operation of multiple valves, as in conventional systems. Particularly the provision of the extension groove extends the range of possible functions providable with the respective ports so that the number of adjustable operation modes manageable with a corresponding fluidic valve can be further increased.

According to the second aspect of the invention, a sample injector is provided which uses only one switchable valve to adjust a desired operation mode selected from a bypass mode, a flush mode and a block mode and a main path mode (such a main pass mode may be activatable in any desired aspect or embodiment of the invention). In the bypass mode, a mobile phase drive and a separation unit forming part of the fluid separation system together with a sample injector are fluidically coupled to one another directly via ports and fluidic paths of the valve. In a main path mode the mobile phase drive is connected to the hydraulic path comprising loop capillary, needle, seat and seat capillary and the latter hydraulic path is connected to the separation unit via ports and fluidic paths of the valve. In a flush mode, needle and/or seat may be flushed, cleaned, washed or rinsed so as to reduce the probability of undesired carryover of sample material from one experiment to the next one. In this context, it may be particularly possible to selectively clean an internal or an external surface of the injection needle which can both be realized using one and the same injection valve. A block mode may be advantageous in order to decouple a complete path of sample loop, needle, seat and seat capillary from the rest of the fluidic system so that neither ambient pressure (particularly atmospheric pressure) nor pressure of the mobile phase drive of the fluid separation system can have a disturbing influence on this fluidic path. It should be said that sudden pressure drops occurring in an uncontrolled manner in this fluidic path may have a deteriorating impact on the function of this group of fluidic members. Thus, by separating such a fluidic section—for instance during the danger of a pressure drop—from the rest of the fluidic system, it is possible to protect such components against damage. It is advantageous that these and other operation modes may all be adjusted by a simple switching of a single valve.

According to the third aspect of the invention, a comprehensive cleaning, rinsing or flushing capability can be provided with a single fluidic valve and a single flush pump. Therefore, a highly compact sample injector can be provided which nevertheless offers the full range of flushing capabilities, i.e. complete flushing of a sample path including sample loop, needle, seat and seat capillary, a back flush mode for a seat for cleaning the seat from sample residues, and a needle wash mode in which an internal and/or an external surface of the needle can be cleaned in a wash port. Thus, issues with undesired carryover of samples can be strongly suppressed according to an exemplary embodiment while at the same time maintaining a very compact sample injector.

In the following, further exemplary embodiments of the switchable valve will be explained. However, these embodiments also apply to the sample injectors, the fluid separation systems and to the methods.

Particularly, the fluidic valve may fulfill the tasks of flushing a metering device, drawing a sample using a metering device, externally washing a needle attached to a loop containing the sample, connecting an injector flow path with a flow delivery system (injection, valve to main path), filling the flush port with fresh solvent, back flushing the seat and seat outside, flushing the full injector flow path, flushing the autosampler. Other tasks like pre-pressurizing the injector flow path to system pressure, de-pressurizing the injector flow path to ambient pressure, or the execution of diagnostic features (for instance test solvent delivery of hydraulic components, tests for leaks, tests for blockage, etc.) can be realized with one and the same fluidic valve. Therefore, the fluidic valve may be used for an autosampler to provide an intelligent link of flow paths with a valve. One single shear valve formed of a stator and the rotor can be sufficient for this according to an exemplary embodiment of the invention. Such a functionality can also be achieved under high pressure of for instance 1200 bar or more.

In an embodiment, the eight circumferential ports are arranged at the same radial distance from the central port. In other words, a circle may be drawn which contacts each of the ports.

In an embodiment, all but one of the eight circumferential ports are spaced from at least one neighbored circumferential port by 45°, and one of the eight circumferential ports is spaced from one of its neighbors by less than 45°, particularly by 22.5°, and from the other one of its neighbors by more than 45°, particularly 67.5°. Thus, the switching procedure may be very simple since most switching steps can be performed with the same angular rotation.

In an embodiment, all but one of the eight circumferential ports have a cylindrical input shape, and a near-to-elliptic outlet shape towards a rotor's side, and the one of the eight circumferential ports having the extension groove is a cylindrical port with an arcuate extension groove, particularly extending by 22.5°. Hence, the rotor side may have a near-to-elliptic output as the cylindrical holes are not perpendicular to the stator's plane. By an arcuate extension of the groove with the shape of a circular section, the extension will always be aligned with a corresponding end section of a fluidic path of the other fluidic member during the rotation.

In an embodiment, the three arcuate fluid paths (which may all have the shape of a circular section) are arranged at the same radial distance with respect to a central end point of the straight fluid path. In an embodiment, the three arcuate fluid paths are arranged at the same radial distance as a radial end point of the straight fluid path. Providing the three arcuate fluidic paths at the same radial distance allows proper fluid communication of such fluidic paths with corresponding ports. This also simplifies fluid communication between the straight fluid path and the various ports.

In an embodiment, two neighbored ones of the three arcuate fluid paths have a radial length of 67.5°, and the third one of the three arcuate fluid paths has a radial length of 45°. This geometry allows for a very easy adjustment of the individual operation modes.

In an embodiment, the valve is a rotary valve, and the first and the second valve members are rotatably movable with respect to each other. Particularly, the valve member having the ports may serve as a stator, whereas the other valve member having the fluidic paths can be the rotor of such a rotary valve.

In an embodiment, one or more of the ports comprise a through hole (through the respective valve member) having an opening fluidly coupling with the fluid path dependent on the moving position. When a fluid path is aligned to one of the ports, fluid communication between these two fluidic structures is enabled, but the sealing with regard to the environment is maintained at the same time.

In an embodiment, the first valve member and the second valve member are configured for fluidly coupling respective ones of the ports in dependency on a relative movement position of the first and second valve members with respect to each other. Therefore, simply moving one of the two valve members relative to the other one allows for the adjustment of the desired operation mode.

In an embodiment, the first valve member is a stator and the second valve member is a rotor configured to be moved with respect to the first valve member. Alternatively, it is also possible to perform a switching by a translatory motion of one of the fluidic members with regard to the other one. In this case, no rotation is necessary, but the valve members are shifted relative to one another.

In an embodiment, the switchable valve comprises a drive for moving the one of the first and second valve members to be moved. Such a drive may be an electric motor allowing to rotate one of the valve members with regard to the other one by a predefinable angular range so that proper and precise alignment between a port and a certain fluidic path can be achieved.

In an embodiment, the switchable valve comprises a valve control unit configured for controlling a movement of the first and second valve members with respect to each other. Such a valve control unit may be a processor, for instance a microprocessor or a central processing unit (CPU).

In an embodiment, the switchable valve is configured to conduct a liquid in the at least one fluid path at a high pressure at which compressibility of the liquid becomes noticeable. In an embodiment, the switchable valve is configured to conduct a liquid in the at least one fluid path at a high pressure in a range of 20-200 MPa, and particularly 50-120 MPa.

A single fluid valve having ports and grooves is sufficient to execute a diagnosis function (in which the device tests whether the functionality of a part or the entire fluidic device works properly, and issues a diagnosis result), provide a bypass function (in which a direct connection between a mobile phase drive and a separation column is provided) via the valve, provide a block function (in which certain sections of a fluidic device are blocked and are fluidically decoupled from ambient pressure and the high pressure of a mobile phase drive), and for providing a flush function (particularly including a back flushing of a seat).

In the following, further exemplary embodiments of the sample injectors will be explained. However, these embodiments also apply to the fluid separation systems, the valve and to the methods.

In an embodiment, the valve is configured to be switchable into a wash mode in which an exterior of the needle is washed. During such a wash mode, the external surface of the needle can be cleaned to remove sample from an earlier experiment or other impurities.

In an embodiment, the valve is configured to be switchable in a sample fluid intake mode in which the sample fluid is intaken into the sample loop via the needle by a metering device. Therefore, it is also possible to use the fluidic valve for a sample intake mode for transferring a sample from a sample reservoir such as a vial or well plate through the needle and into a part of the capillary of the sample injector. The metering device may be a pump which is provided for applying a negative pressure in order to draw in the sample in a syringe-like way.

In an embodiment, the valve is configured to be switchable in a diagnosis mode in which a selectable fluidic part of the fluid separation system is diagnosable, particularly with respect to blockage or leakage. Diagnosing may imply a switch of the valve so that a specific fluidic part can be inspected. For this purpose, it is also possible to arrange one or more sensors within the fluidic paths to provide the respective information, for instance with regard to flow rate or pressure.

In an embodiment, the valve is configured to be switchable in a sample fluid injection mode in which the sample fluid is injected into a fluidic channel between the mobile phase drive and the separation unit. Such a sample fluid injection mode may transfer a previously intaken sample into an actual sample separation path between mobile phase drive and chromatographic column where the actual separation is carried out.

In an embodiment, the sample injector further comprises a metering device in fluid communication with two ports of the valve and configured for introducing a metered amount of the sample fluid on the sample loop, wherein the valve is configured to be switchable so that in the block mode the valve fluidically decouples also the metering device from the mobile phase drive and from ambient pressure. Hence, also the metering syringe may be part of the fluidic part which can be decoupled from an environment in the block mode.

In an embodiment, the valve is configured to be switchable so that the valve enables back flushing of the seat in the flush mode. Back flushing may denote a process of flushing the seat with a fluid flow direction which is opposite to a fluid flow direction during a transfer of the sample from the sample loop to a path between the mobile phase drive and the separation column. Back flushing is a way of efficiently cleaning the seat.

In an embodiment, the sample injector further comprises a flush pump, particularly exactly one flush pump, in fluid communication with a port of the valve and configured for flushing of at least one of the group consisting of the needle and the seat. Particularly in an embodiment in which exactly one flush pump is combined with exactly one fluidic valve in a sample injector, a very compact device is obtained.

In an embodiment, the sample injector further comprises a wash port in fluid communication with a port of the valve and configured for washing the needle, particularly for washing selectively an exterior surface of the needle or an interior surface of the needle. The wash port is configured so that the needle can be immersed therein for cleaning an external and/or an internal needle surface to suppress carryover. In an embodiment, the needle wash mode comprises at least one of the group consisting of an external needle wash mode in which an external surface of the needle is washed in the wash port, and an internal needle wash mode in which an internal surface of the needle is washed in the wash port.

In an embodiment, the valve is configured to be switchable so as to activate at least one selected of the following operation modes: a) a bypass mode in which the valve fluidically couples the mobile phase drive with the separation unit via the valve; b) a block mode in which the valve fluidically decouples at least the sample loop, the needle, the seat and the seat capillary from the mobile phase drive and ambient pressure; c) a sample fluid intake mode in which the sample fluid is intaken into the sample loop via the needle driven by a metering device in fluid communication with two ports of the valve and configured for introducing a metered amount of the sample fluid on the sample loop; d) a diagnosis mode in which a selectable fluidic part of the fluid separation system is diagnosable, particularly with respect to at least one of the group consisting of blockage and leakage; e) a sample fluid injection mode in which the sample fluid is injected into a fluidic channel between the mobile phase drive and the separation unit. Therefore, many different operation modes may be adjusted with one and the same valve.

The valve can be a shear valve being preferably configured to conduct a liquid in the at least one fluid path at a high pressure at which compressibility of the liquid becomes noticeable, such as pressure in the range of 20-200 MPa, and particularly 50-120 MPa.

The shear valve might be embodied in an HPLC sample injector configured to introduce a sample fluid into a mobile phase. The mobile phase is to be driven by a mobile phase drive through a separation unit for separating compounds of the sample fluid in the mobile phase. A sample loop is provided for receiving the sample fluid. The shear valve is provided for switching the sample loop between the mobile phase drive and the separation unit for introducing the sample fluid into the mobile phase.

Embodiments of the present invention might be embodied based on most conventionally available HPLC systems, such as the Agilent 1200 Series Rapid Resolution LC system or the Agilent 1100 HPLC series (both provided by the applicant Agilent Technologies—see www.agilent.com—which shall be incorporated herein by reference).

One embodiment comprises a pumping apparatus having a piston for reciprocation in a pump working chamber to compress liquid in the pump working chamber to a high pressure at which compressibility of the liquid becomes noticeable.

One embodiment comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (for instance from the supply), thus allowing to provide a continuous flow at the output. However, it is clear that also both pumping apparatuses might be operated in parallel (i.e. concurrently), at least during certain transitional phases for instance to provide a smooth(er) transition of the pumping cycles between the pumping apparatuses.

The separating device preferably comprises a chromatographic column (see for instance http://en.wikipedia.org/wiki/Column_chromatography) providing the stationary phase. The column might be a glass or steel tube (for instance with a diameter from 50 µm to 5 mm and a length of 1 cm to 1 m) or a microfluidic column (as disclosed for instance in EP 1577012 or the Agilent 1200 Series HPLC-Chip/MS System provided by the applicant Agilent Technologies, see for instance http://www.chem.agilent.com/Scripts/PDS.asp?lPage=38308). For example, a slurry can be prepared with a powder of the stationary phase and then poured and pressed into the column. The individual components are retained by the stationary phase differently and separate from each other while they are propagating at different speeds through the column with the eluent. At the end of the column they elute one at a time. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface, though in EBA a fluidized bed is used.

The mobile phase (or eluent) can be either a pure solvent or a mixture of different solvents. It can be chosen for instance to minimize the retention of the compounds of interest and/or the amount of mobile phase to run the chromatography. The mobile phase can also been chosen so that the different compounds can be separated effectively. The mobile phase might comprise an organic solvent like for instance methanol or acetonitrile, often diluted with water. For gradient operation water and organic is delivered in separate bottles, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The pressure in the mobile phase might range from 2-200 MPa (20 to 2000 bar), in particular 10-150 MPa (100 to 1500 bar), and more particular 50-120 MPa (500 to 1200 bar).

The HPLC system might further comprise a sampling unit for introducing the sample fluid into the mobile phase stream, a detector for detecting separated compounds of the sample fluid, a fractionating unit for outputting separated compounds of the sample fluid, or any combination thereof. Further details of HPLC system are disclosed with respect to the Agilent 1200 Series Rapid Resolution LC system or the Agilent 1100 HPLC series, both provided by the applicant Agilent Technologies, under www.agilent.com which shall be in cooperated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 (compare the detailed description of FIG. 2 to FIG. 9) can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

Figure 1:
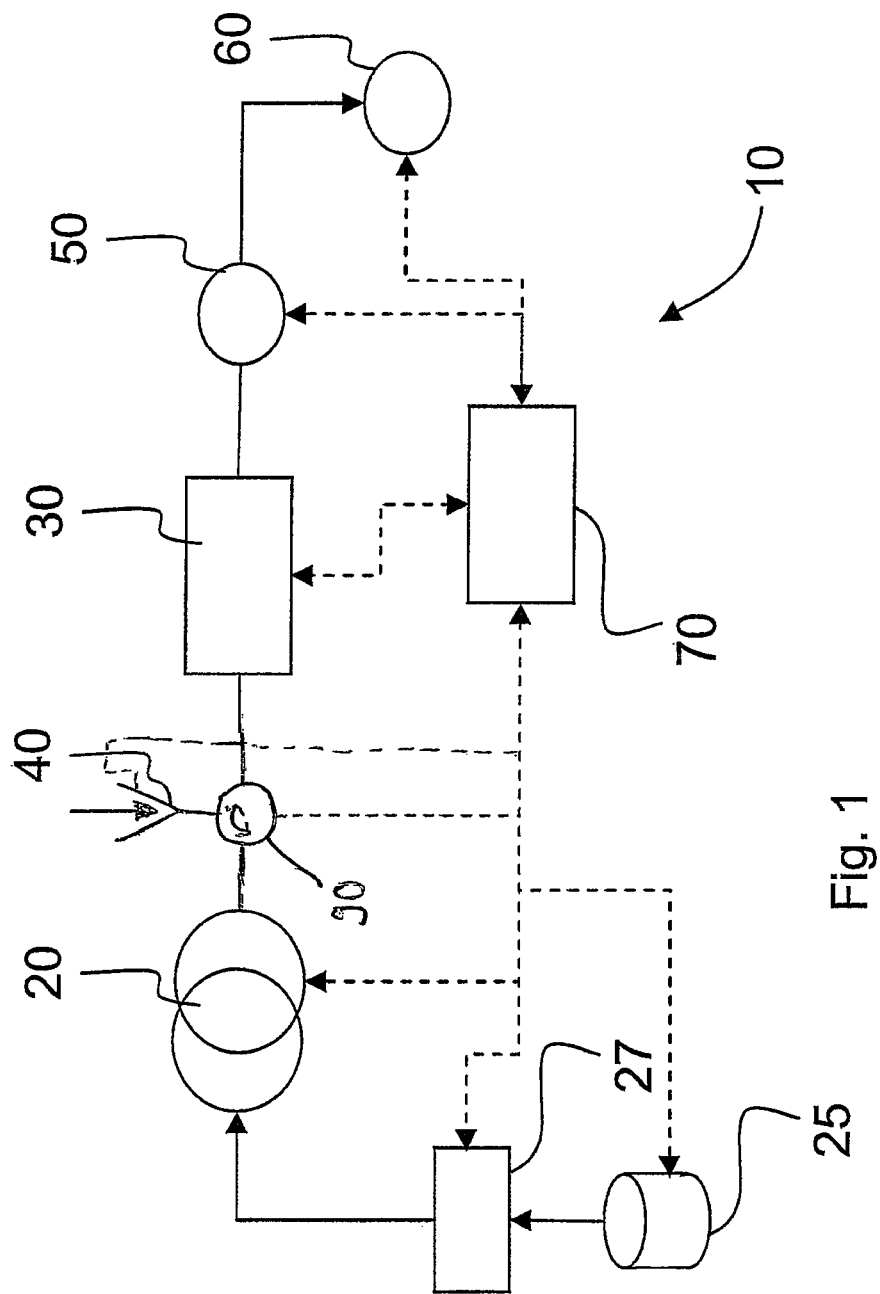
FIG. 1 shows a liquid separation system, in accordance with embodiments of the present invention, for instance used in high performance liquid chromatography (HPLC).

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (for instance setting control parameters) and receive therefrom information regarding the actual working conditions (such as output pressure, flow rate, etc. at an outlet of the pump). The data processing unit 70 might also control operation of the solvent supply 25 (for instance setting the solvent/s or solvent mixture to be supplied) and/or the degasser 27 (for instance setting control parameters such as vacuum level) and might receive therefrom information regarding the actual working conditions (such as solvent composition supplied over time, flow rate, vacuum level, etc.). The data processing unit 70 might further control operation of the sampling unit 40 (for instance controlling sample injection or synchronization sample injection with operating conditions of the pump 20). The separating device 30 might also be controlled by the data processing unit 70 (for instance selecting a specific flow path or column, setting operation temperature, etc.), and send—in return—information (for instance operating conditions) to the data processing unit 70. Accordingly, the detector 50 might be controlled by the data processing unit 70 (for instance with respect to spectral or wavelength settings, setting time constants, start/stop data acquisition), and send information (for instance about the detected sample compounds) to the data processing unit 70. The data processing unit 70 might also control operation of the fractionating unit 60 (for instance in conjunction with data received from the detector 50) and provides data back.

Reference numeral 90 schematically illustrates a switchable valve which is controllable for selectively enabling or disabling specific fluidic paths within apparatus 10. An example of the constitution of such a valve will be explained in the following in more detail.

Figure 2:
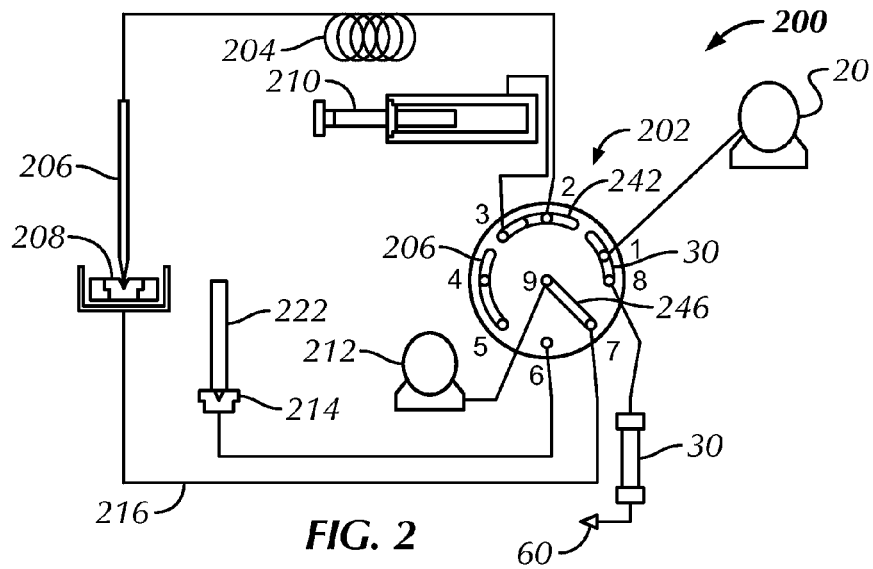
FIG. 2 shows a sample injector according to an exemplary embodiment of the invention together with a fluidic valve thereof, wherein also a fluidic coupling between the sample injector and a mobile phase drive and a chromatographic separation column is shown.

FIG. 2 illustrates a sample injector 200 having a corresponding valve 202 according to an exemplary embodiment of the invention. The sample injector 200 may be implemented in the fluid separation system 10 (having particularly the mobile phase drive 20 and the separation column 30) shown in FIG. 1 for separating compounds of a sample fluid in a mobile phase.

Furthermore, a sample loop 204 is provided as part of the sample injector 200, being in fluid communication with a port 2 of the valve 202, and being configured for receiving the sample fluid via an injection needle 206 which in turn receives the fluid from a vial (not shown in FIG. 2) as will be described below in more detail. The needle 206 is in fluid communication with the sample loop 204. A seat 208 is provided and is configured for selectively receiving the needle 206 in a fluid-tight manner. Furthermore, a seat capillary 216 is provided which is in fluid communication with the seat 208 and is in fluid communication with a port 7 of the valve 202. Furthermore, a metering device 210 is shown which is in fluid communication with a port 3 of the fluidic valve 202 and with a port 5 of the fluidic valve 202. A flush pump 212 (such as a 50 bar flush pump) is in fluid communication with a port 9 in a center of the fluidic valve 202. Furthermore, a wash port 214 is provided which participates during a needle wash procedure. Dual function wash port 214 is capable for performing an external needle wash, or can also be operated to provide for a flow path connection of the needle 206 to a wash line.

Valve 202 has nine ports each of which being connected or connectable to a respective fluidic member to provide fluid communication therewith: Port 1 of the fluidic valve 202 is connected to the mobile phase drive 20, port 2 is connected to the loop capillary 204, port 3 and port 5 are connected to the metering pump 210, port 4 is disconnected in the shown operation mode, port 6 is connected to the wash port 214, port 7 is connected to the seat 208, port 8 is connected to the separation column 30 and port 9 is connected to the flush pump 212.

The needle 206 can be moved between the seat 208 and a vial (not shown in FIG. 2) by an electric motor or another drive unit (not shown in FIG. 2). When the needle 206 is immersed in the vial, the metering pump 210 can apply an underpressure to the needle 206 so that the fluidic sample is sucked via the needle 206 into the loop capillary 204. Subsequently, the needle 206 is driven back into the seat 208 and the injected fluid is transferred from the sample loop 204 through the seat 208 and the valve 202 into a fluidic path between the mobile phase drive 20 and the separation column 30. All the different operation modes involved during this procedure can be carried out by a corresponding switching operation of the fluidic valve 202.

Figure 3:
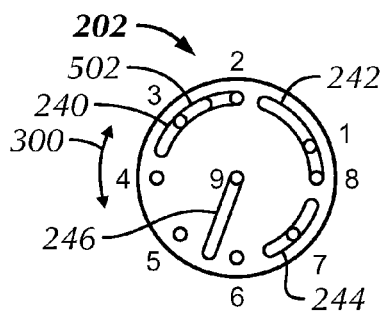
FIG. 3 is an illustration of the injection valve of FIG. 2 in one operation mode.
Figure 4:
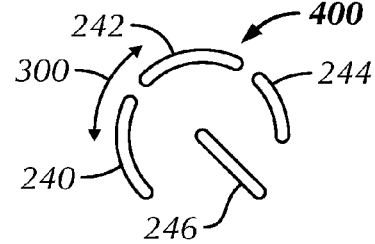
FIG. 4 illustrates a rotor member of the valve of FIG. 3.
Figure 5:
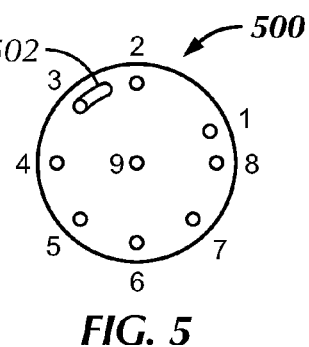
FIG. 5 illustrates a stator member of the valve of FIG. 3.

FIG. 3 to FIG. 5 illustrate constitution of switchable valve 202 in more detail.

FIG. 3 shows valve 202 of FIG. 2 in another switching state. Valve 202 is constituted by a rotor member 400 shown in FIG. 4 and by a stator member 500 shown in FIG. 5. The rotor member 400 and the stator member 500 are assembled to form the valve 202 and are rotatable (see arrow 300 in FIG. 3 and FIG. 4) relative to one another in such a manner that different operation modes of the fluidic valve 202 can be adjusted.

The stator member 500 has the nine cylindrical ports denoted with numerals 1 to 9 in FIG. 5 and extending perpendicular to the paper plane of FIG. 3 and FIG. 5. The ports 1 to 9 of the stator member 500 comprise eight circumferential cylindrical ports 1 to 8 distributed along a circumference of the stator member 500. One central port 9 is arranged at a central position of the stator member 500. Moreover, circumferential port 3 has also an extension groove 502, as best seen in FIG. 5. Therefore, a groove etched in a surface of the stator member 500 is directly fluidically connected to the cylindrical port 3 extending perpendicularly to the paper plane of FIG. 5. Hence, the injection valve 202 has the eight outside ports 1 to 8 and one center port 9. Each of the ports 1 to 9 represents a port where a capillary can be connected to. Reference numeral 502 represents a groove engraved into the stator member 500. The eight circumferential ports 1 to 8 are arranged at the same radial distance from the central port 9. All but port 1 of the circumferential ports 1 to 8 are spaced from a respective neighbored circumferential port 1 to 8 by 45°. Port 1, however, is spaced from neighbor port 8 by 22.5° and from neighbor port 2 by 67.5°. The arcuate extension groove 502 extends along a radial angle of 22.5°.

The rotor member 400 has a first groove as a first fluidic path 240 (which may also be denoted as metering input groove), a second groove as a second fluidic path 242 (which may also be denoted as a bypass groove), a third groove as a third fluidic path 244 (which may also be denoted as a sample outlet groove) and a fourth groove as a fourth fluidic path 246. Hence, the rotor valve member 400 has the four fluidic paths 240, 242, 244, 246 provided as grooves in a substrate of the rotor member 400 which serve for fluidically coupling respective one of the ports 1 to 9 in dependency on a relative movement position of the valve members 400, 500 with respect to each other. More specifically, the rotor member 400 comprises three arcuate (or curved) fluid paths 240, 242, 244 each being arcuate so as to be fluidically couplable with at least two of the circumferential ports 1 to 8. Moreover, one straight (or linear) fluid path 246 is provided which extends between the central position and a circumferential position so as to be fluidically couplable with a central port 9 and with one of the eight circumferential ports 1 to 8 at a time. The arcuate structures 240, 242, 244 and the straight structure 246 of FIG. 4 each represent a groove that combines stator ports 1 to 9. The three arcuate fluidic paths 240, 242, 244 are arranged at the same radial distance with respect to the central end point of the straight fluid path 246. Two neighbored ones of the three arcuate fluidic paths, i.e. fluidic paths 240 and 242 have a radial length of 67.5°. The third one of the three arcuate fluidic paths, i.e. fluidic path 244, has a radial length of 45°.

However, it should be said that the given positions and angles of the various ports and grooves may vary in other embodiments without departing from the scope of the invention.

Figure 6:
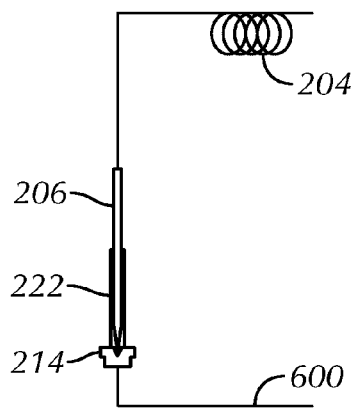
FIG. 6 shows a flush port operated for flushing an internal surface of an injection needle coupled to a loop capillary and for enabling fluid path so that seat back flushing is possible by setting the injection valve into the correct position.
Figure 7:
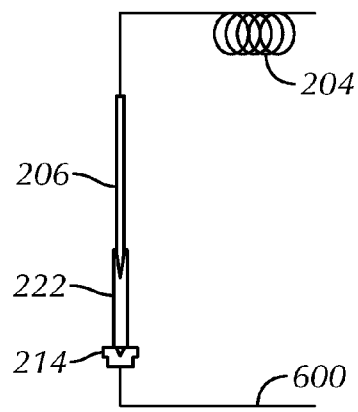
FIG. 7 illustrates a flush port operated for flushing an external surface and the internals of the needle connected to a loop capillary and for refilling the flush port with fresh solvent.

A needle accommodation 222 shown in FIG. 6 and FIG. 7 as well as in FIG. 2 cooperates with the wash port 214 to enable washing of the needle 206. FIG. 6 shows a first operation mode in which the needle 206 is sealed in the wash port 214 for connecting the loop capillary 204 above with another flow path 600 underneath flush port or wash port 214. In contrast to this, in FIG. 7, the needle 206 is shown in an open position to flush its external surface. Therefore, the flush port 214 can also make a connection between needle 206 and a capillary.

In the following, referring to FIG. 8 to FIG. 16, operation of the sample injector 200 in an operation mode strongly suppressing undesired carryover of sample material will be explained. This enables a combined seat back flushing and an inner needle and loop flushing with up to three solvents (two wash solvents, one reconditioning). External needle wash can be performed with up to three solvents as well. A pre-/decompress loop feature is provided as well.

Figure 8:
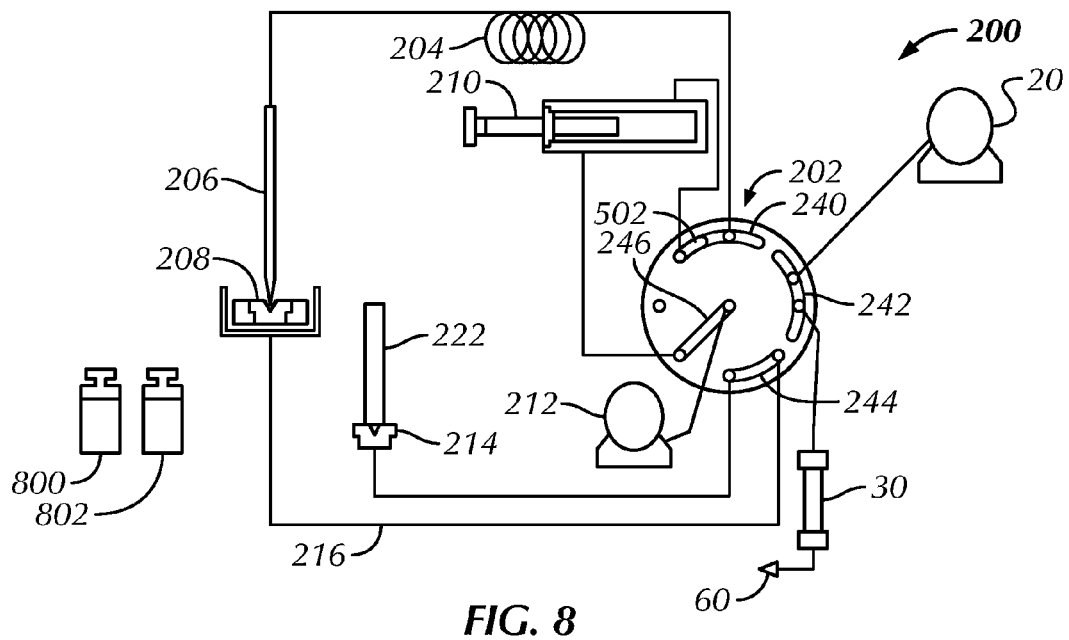
FIG. 8 shows a sample injector according to an exemplary embodiment of the invention in a bypass mode.

FIG. 8 shows the sample injector 200 in a bypass mode. In this bypass mode, the mobile phase drive 20 (also denoted as analytical pump) is directly fluidically connected via two ports and one groove 242 of the valve 202 with the separation column 30. FIG. 8 also shows that a first vial 800 and a second vial 802 are provided which accommodate liquids which can later be used for the purpose of sample intake or flush fluid intake. Hence, FIG. 8 shows a bypass mode in which the valve 202 fluidically couples the mobile phase drive 20 with the separation unit 30 via the valve 202.

Figure 9:
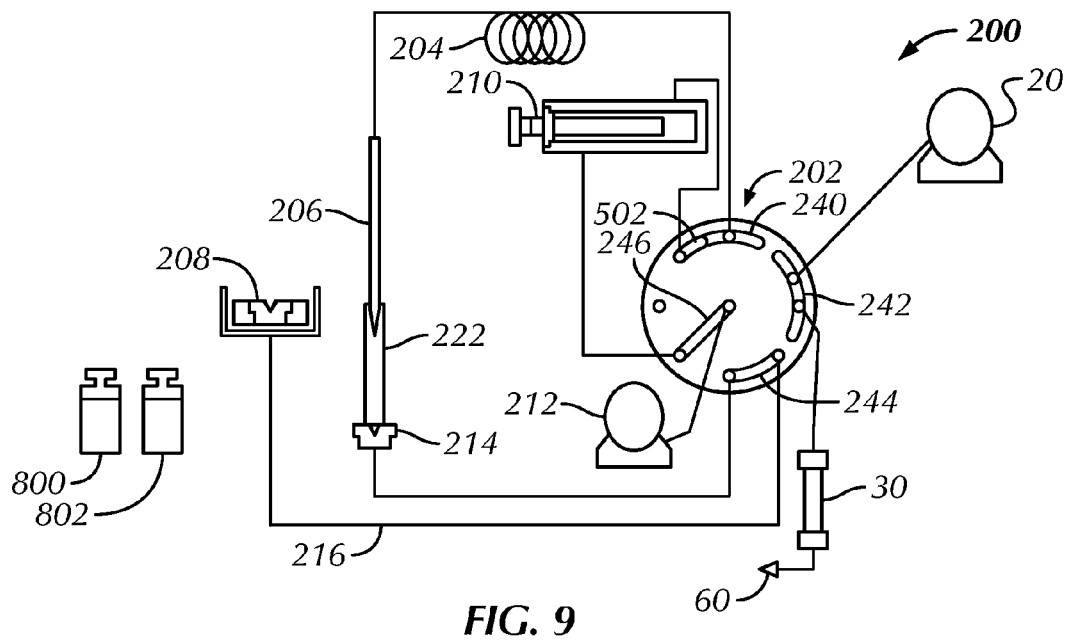
FIG. 9 shows the sample injector of FIG. 8 still in a bypass mode.

In FIG. 9, the sample injector 200 is still in the bypass mode, i.e. mobile phase can flow from mobile phase drive 20 via valve 202 into separation column 30. However, the injection needle 206 which has in FIG. 8 been fluid-tightly received within seat 208 has now been driven into flush capillary or needle accommodation 222 (as in FIG. 7). In the operation mode corresponding to FIG. 9, it is possible to perform an external needle wash (no flow), or an external and an internal needle wash with a strong solvent. Hence, FIG. 9 shows a combined bypass and flush mode in which the valve 202 enables flushing of the needle 206.

Figure 10:
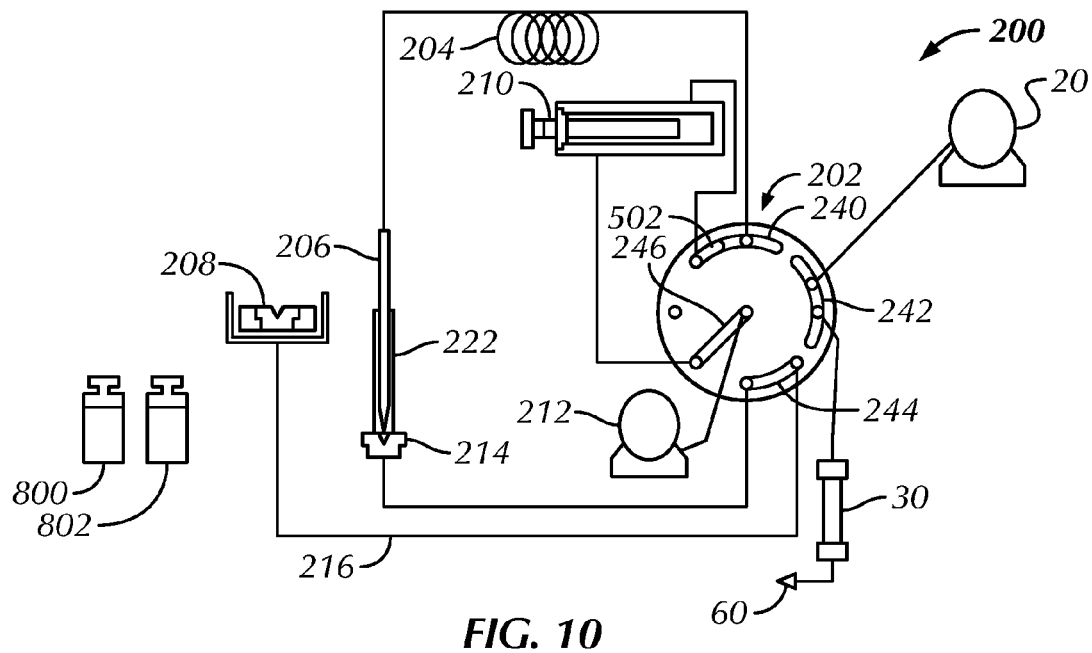
FIG. 10 shows the sample injector of FIG. 8 still in a bypass mode.

As can be taken from FIG. 10, it is also possible to provide, in the bypass mode, a needle seat back flush and an inner needle wash with a strong solvent and with reconditioning solvent. It is also possible to have more than one strong solvent. The injection needle 206 has now been fully driven into flush capillary or needle accommodation 222 and contacts the wash port 214 (as in FIG. 6). Hence, FIG. 10 shows a combined bypass and flush mode in which the valve 202 also enables internal flushing of the needle 206 as well as back flushing of the seat 208.

Figure 11:
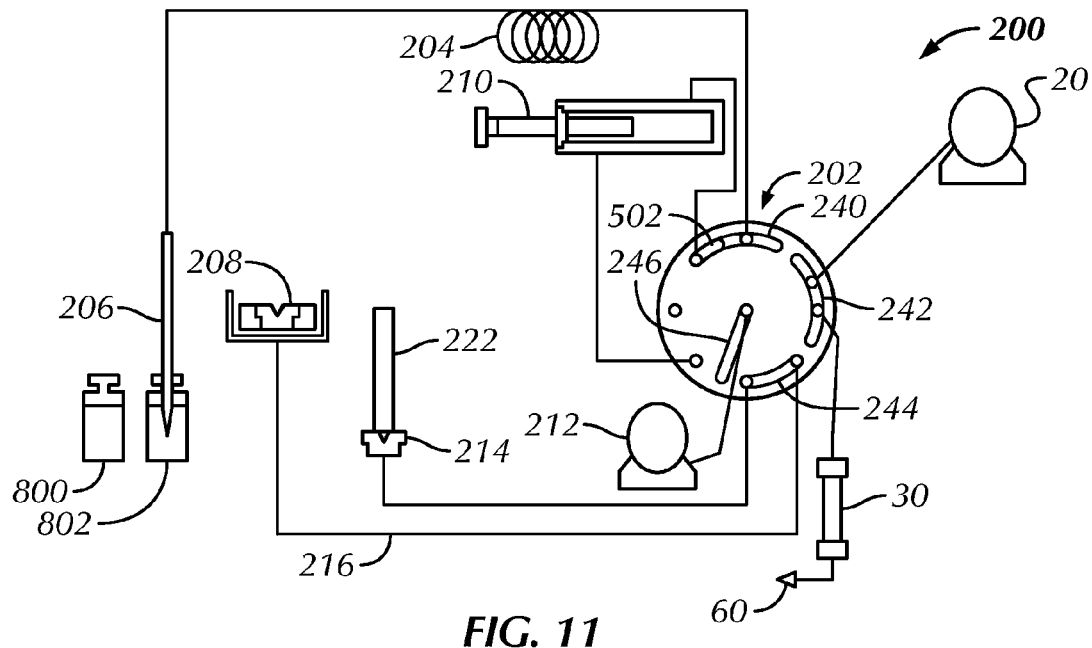
FIG. 11 shows the sample injector of FIG. 8 in a block position.

FIG. 11 now shows the sample injector 200 in a block position, in which sample fluid is drawn. For this purpose, needle 206 has been driven to a position to immerse into vial 802. Under control of the metering pump 210, a defined amount of sample may now be intaken via needle 206 into loop capillary 204. The block position shown in FIG. 11 has been adjusted by rotating valve 202.

Figure 12:
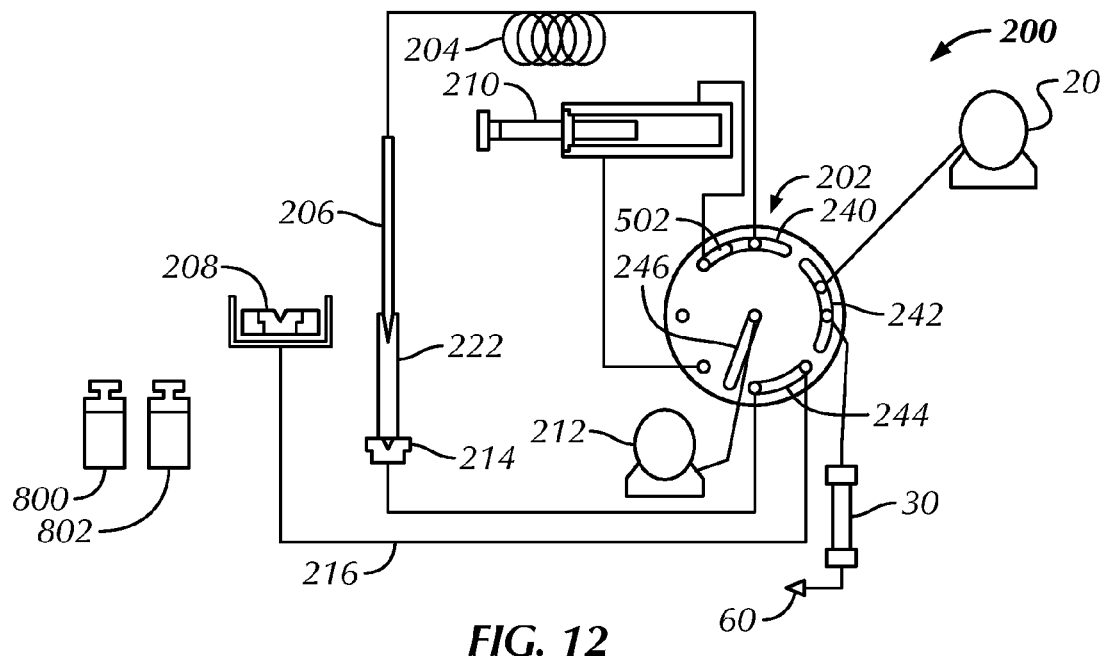
FIG. 12 shows the sample injector of FIG. 8 still in a block position.

FIG. 12 now shows an optional procedure according to a block position in which an external needle wash with a strong solvent can be carried out.

Figure 13:
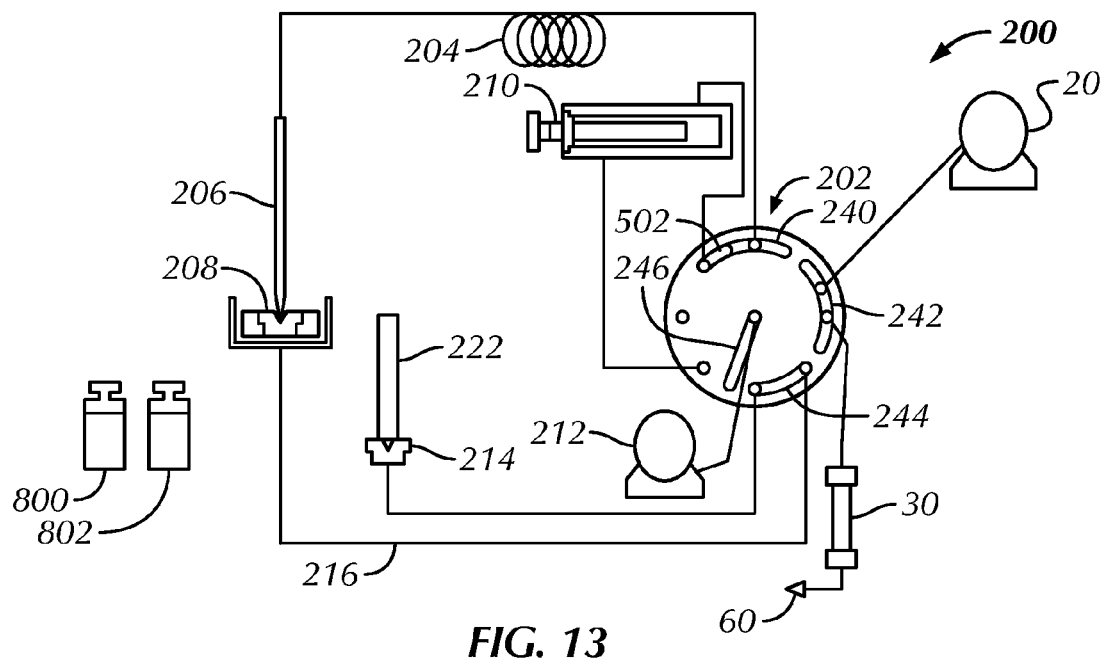
FIG. 13 shows the sample injector of FIG. 8 still in a block position.

FIG. 13 shows a block position in which the metering device 210, the loop capillary 204, the injection needle 206, the seat 208 and the seat capillary 216 are fluidically coupled to one another and are at the same time fluidically decoupled with regard to the mobile phase pump 20 and the ambient pressure, i.e. a surrounding pressure (atmospheric pressure) in the lab in which the apparatus is located. Hence, the ambient pressure may denote the pressure in the environment of the lab. By fluidically isolating the described path, the path is also protected against a pressure drop which may occur during a switching of the valve 202 for injecting the sample into the path between mobile phase drive 20 and chromatographic separation column 30. Hence, FIG. 13 shows a block mode in which the valve 202 fluidically couples the metering device 210, the sample loop 204, the needle 206, the seat 208 and the seat capillary 216 to one another and fluidically decouples the metering device 210, the sample loop 204, the needle 206, the seat 208 and the seat capillary 216 from the mobile phase drive 20 and from ambient pressure.

Figure 14:
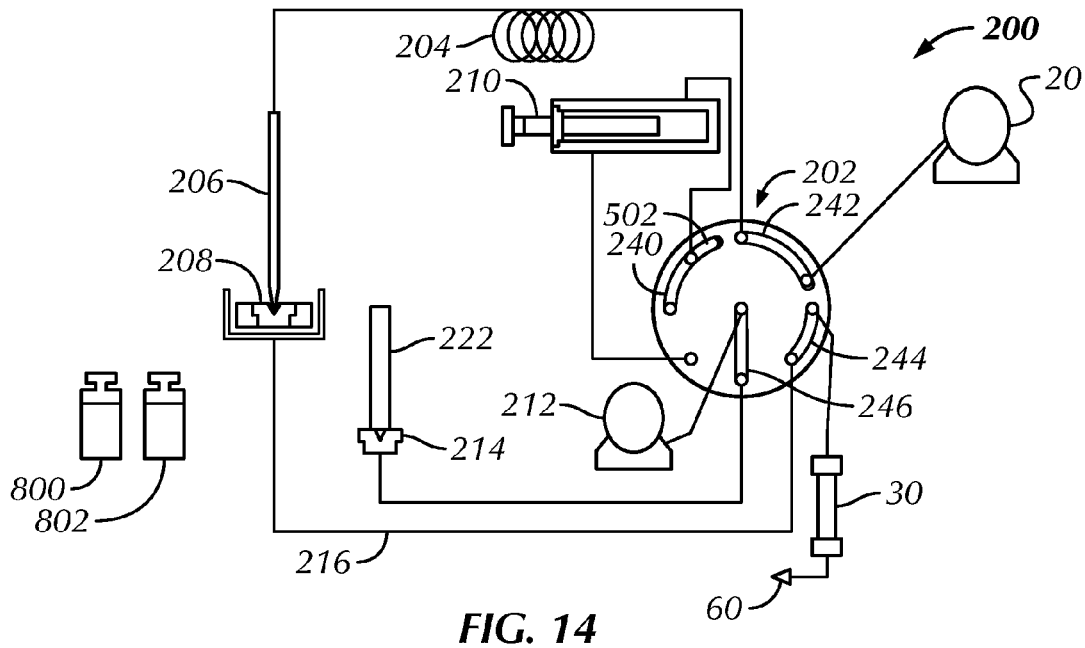
FIG. 14 shows the sample injector of FIG. 8 in a main pass mode.

FIG. 14 shows the sample injector 200 in a main pass mode. In this operation mode, the sample is injected into the fluidic path between mobile phase drive 20 and chromatographic separation column 30. As can be taken from FIG. 14, due to the switching of the valve 202, a continuous fluidic path is formed from the mobile phase drive 20 through the loop capillary 204 (having loaded the fluidic sample), the needle 206, the seat 208, the seat capillary 216, the valve 202 and the chromatographic column 30. Hence, the fluidic sample to be separated is now pumped from the pump 20 to the separation column 30.

Figure 15:
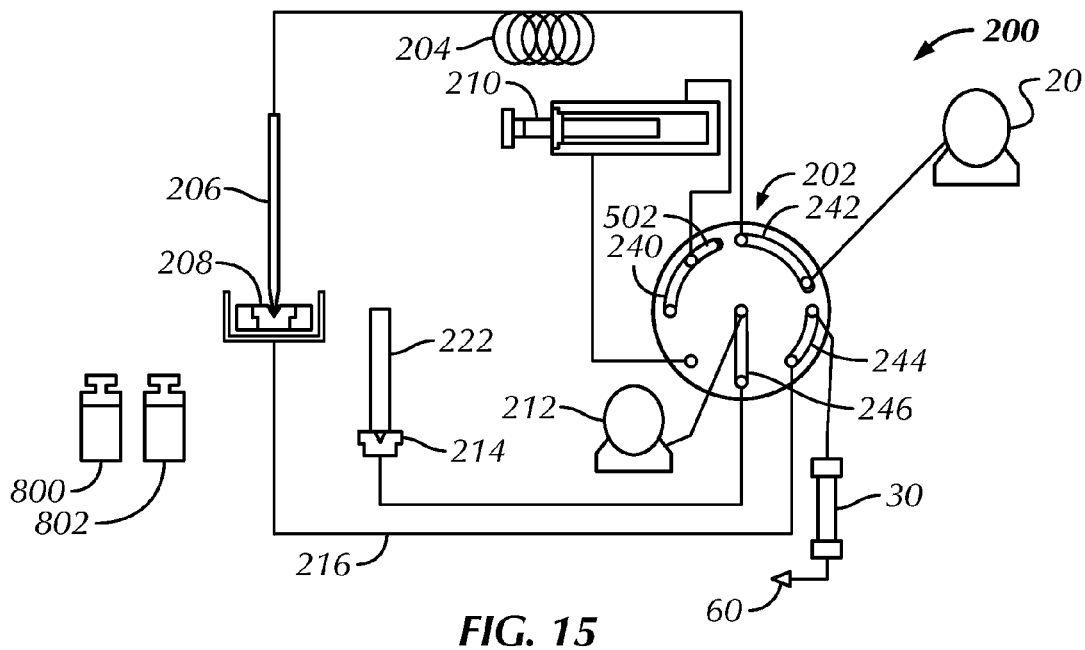
FIG. 15 shows the sample injector of FIG. 8 still in a main pass mode.

FIG. 15 still shows the main pass mode of the sample injector 200, however also shows a flush port refill with a strong solvent.

FIG. 16 again shows the system in a block position, in which the loop 204 and the syringe 210 are de-pressurized. Between FIG. 15 and FIG. 16, the fluidic valve 202 has again been rotated.

Figure 16:
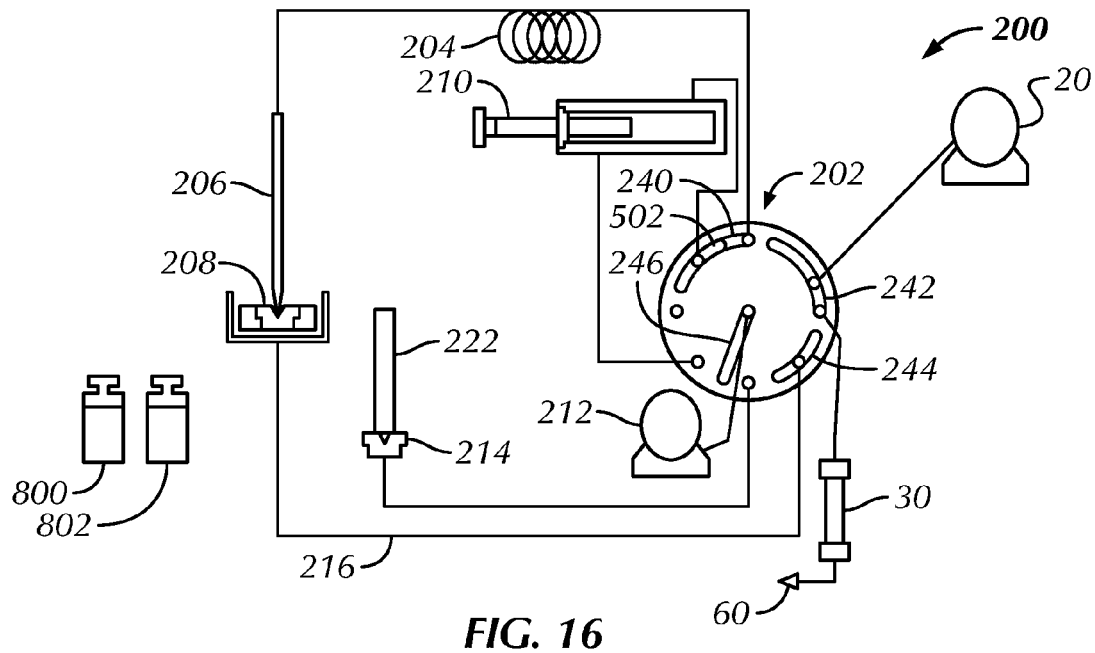
FIG. 16 shows the sample injector of FIG. 8 in a block position.

After the operation mode of FIG. 16, the system can continue in the bypass mode shown in FIG. 7. Therefore, a continuous cyclic procedure cycle is possible.

Referring to FIGS. 17 to 22, a standard injection mode of the sample injector 200 will be explained. This can also be denoted as a stay in main pass mode. Seat back flushing is possible with up to three solvents. An external needle wash (no flow) can be performed with one solvent. A pre-/decompress loop feature is provided as well.

Figure 17:
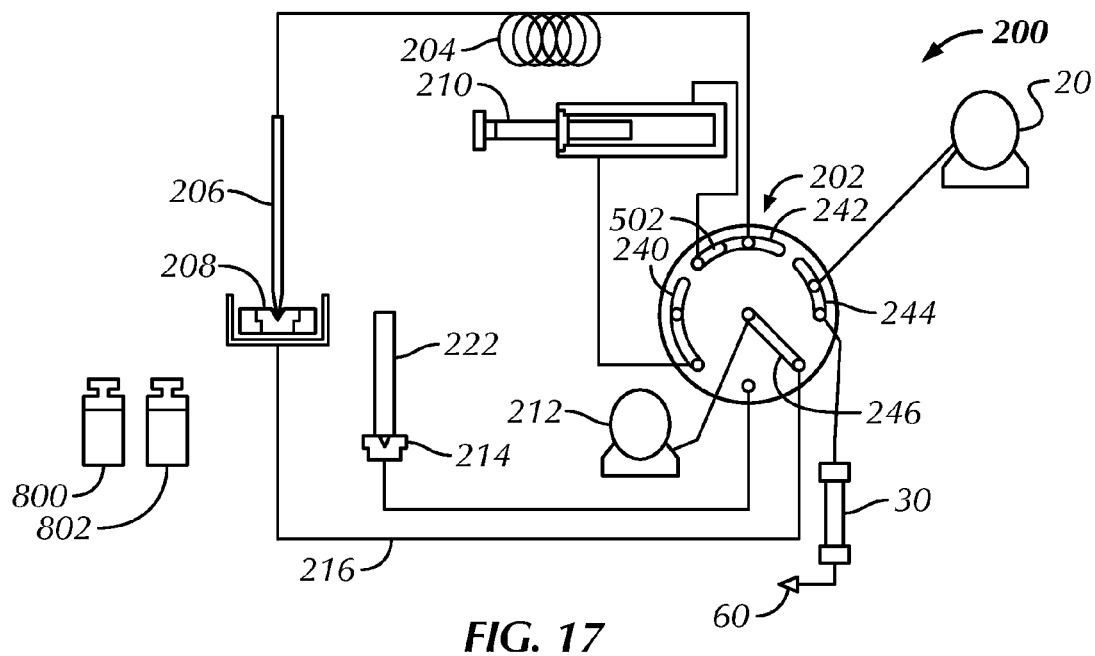
FIG. 17 shows a sample injector operated according to another exemplary embodiment in a bypass mode.

FIG. 17 shows a bypass mode in which a mobile phase can be pumped directly from mobile phase drive 20 through injection valve 202 towards separation column 30.

Figure 18:
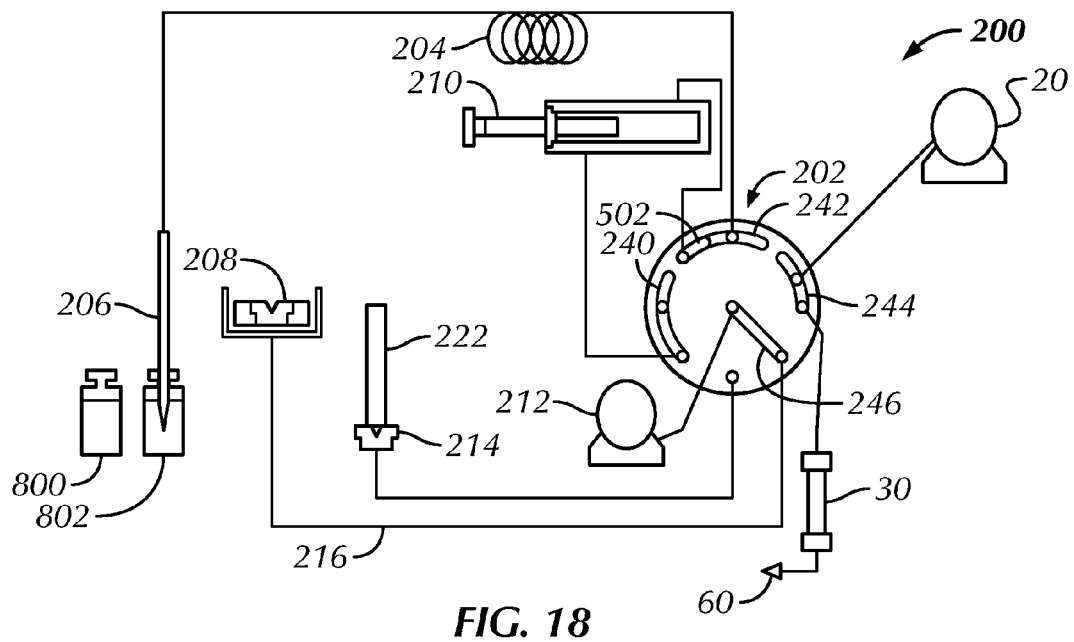
FIG. 18 shows the sample injector of FIG. 17 still in a bypass mode.

FIG. 18 still shows a bypass mode, but now the sample is drawn in from the vial 802 into the loop capillary 204, as described above. At the same time, a back flush of the seat 208 can be carried out via a fluidic path from the flush pump 212 via the injection valve 202, the seat capillary 216 and the seat 208.

Figure 19:
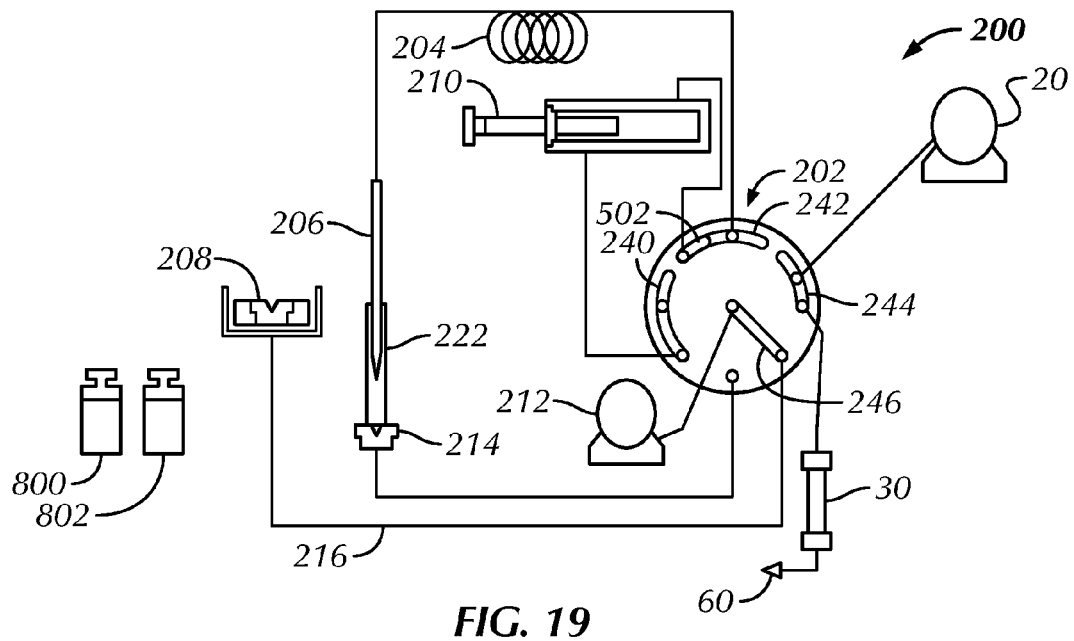
FIG. 19 shows the sample injector of FIG. 17 still in a bypass mode.

FIG. 19 still shows a bypass mode, still with a needle seat back flush, and also with an external needle wash without flow. For the later purpose, the injection needle 206 is now driven into the wash capillary or needle accommodation 222.

Figure 20:
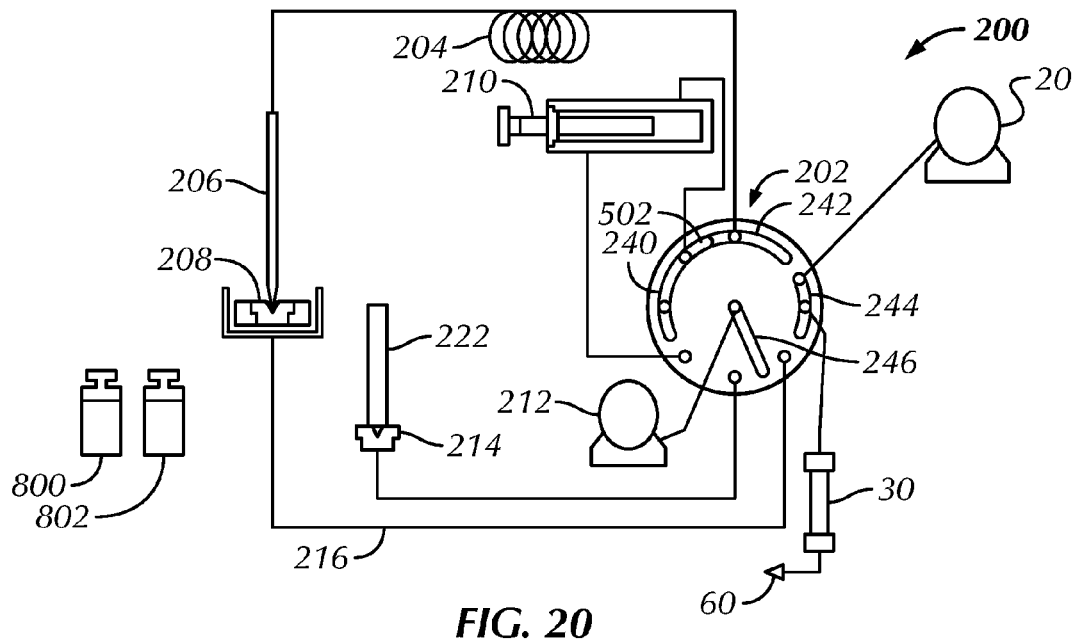
FIG. 20 shows the sample injector of FIG. 17 still in a bypass mode.

In FIG. 20, the system is still the bypass mode, but now the loop 204 is pre-pressurized.

Figure 21:
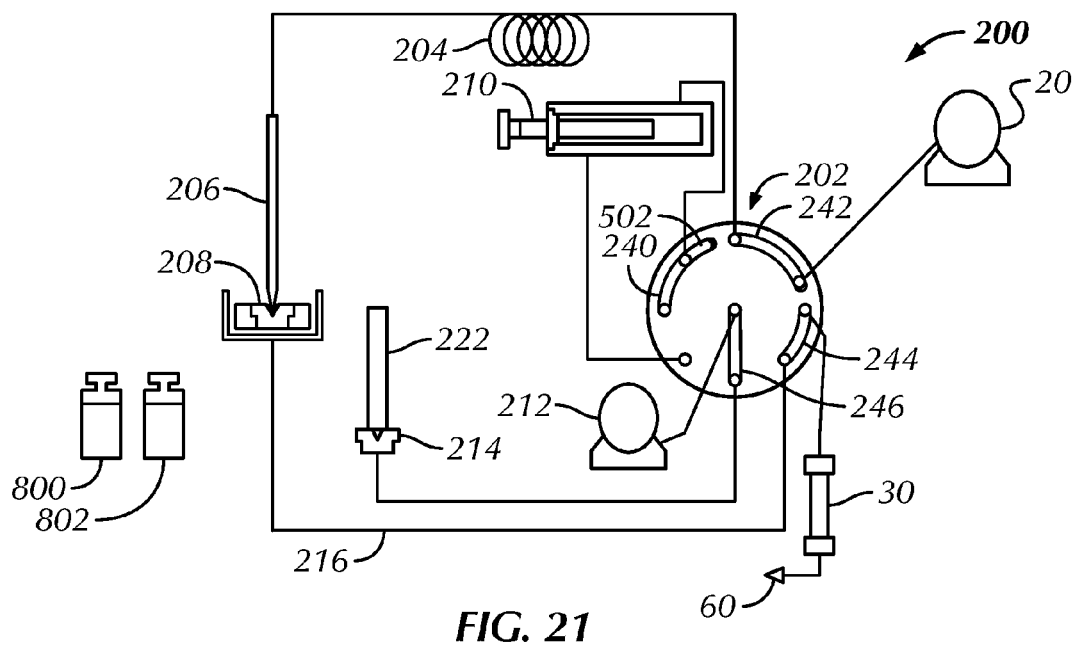
FIG. 21 shows the sample injector of FIG. 17 in a main pass mode.

In FIG. 21, a main pass mode is shown, wherein the injection of the intaken fluidic sample is now carried out from the sample injector 200 into the fluidic path between mobile phase drive 20 and separation column 30. The flush port or wash port 214 may be refilled now.

Figure 22:
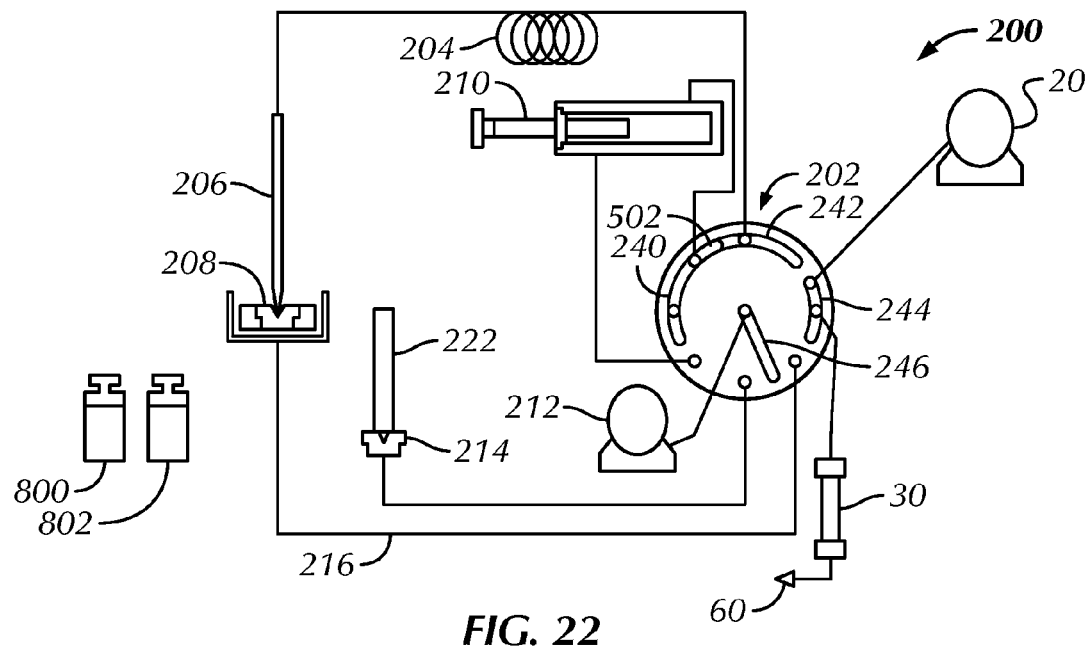
FIG. 22 shows the sample injector of FIG. 17 in a right block position.

FIG. 22 shows a right block position, in which loop 204 and metering device 210 (syringe) can be de-pressurized.

After FIG. 22, the system can start again at the operation mode of FIG. 17, i.e. the bypass mode. Therefore, a continuous cyclic procedure can be carried out.

In the following, referring to FIG. 23 to FIG. 30, diagnostic features will be explained which can be used by sample injector 200.

Figure 23:
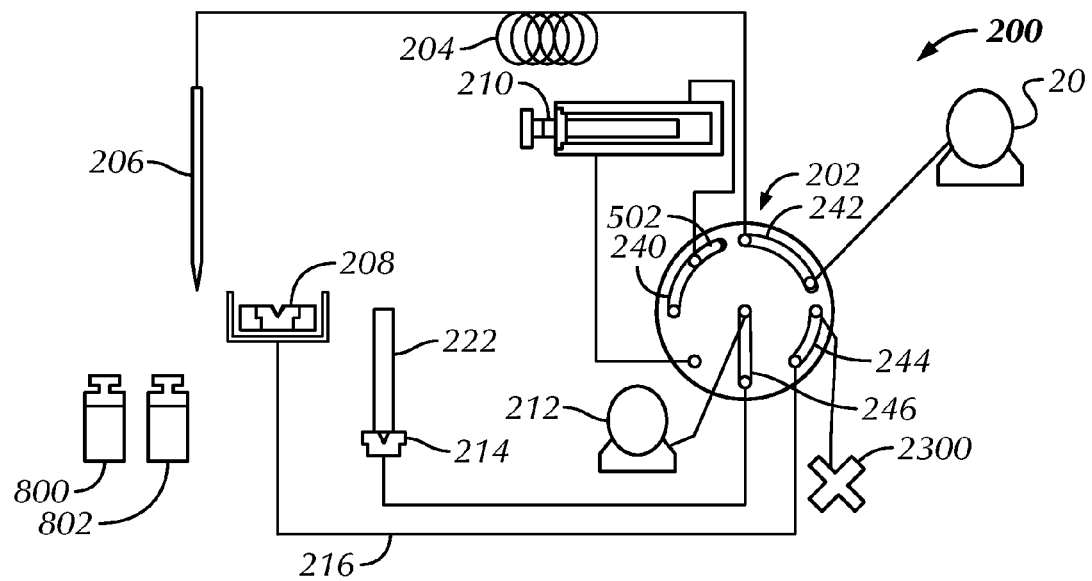
FIG. 23 shows a sample injector operated according to an exemplary embodiment of the invention to provide a diagnostic task by performing a blockage test.

In FIG. 23, it is shown that the chromatographic separation column 30 has been removed, see reference numeral 2300. FIG. 23 now shows a test of needle 206 and loop capillary 204. The mobile phase drive 20 can pump a mobile phase through valve 202, sample loop 204 and needle 206. Thus, these components can be tested with regard to the functionality, leakage, etc.

Figure 24:
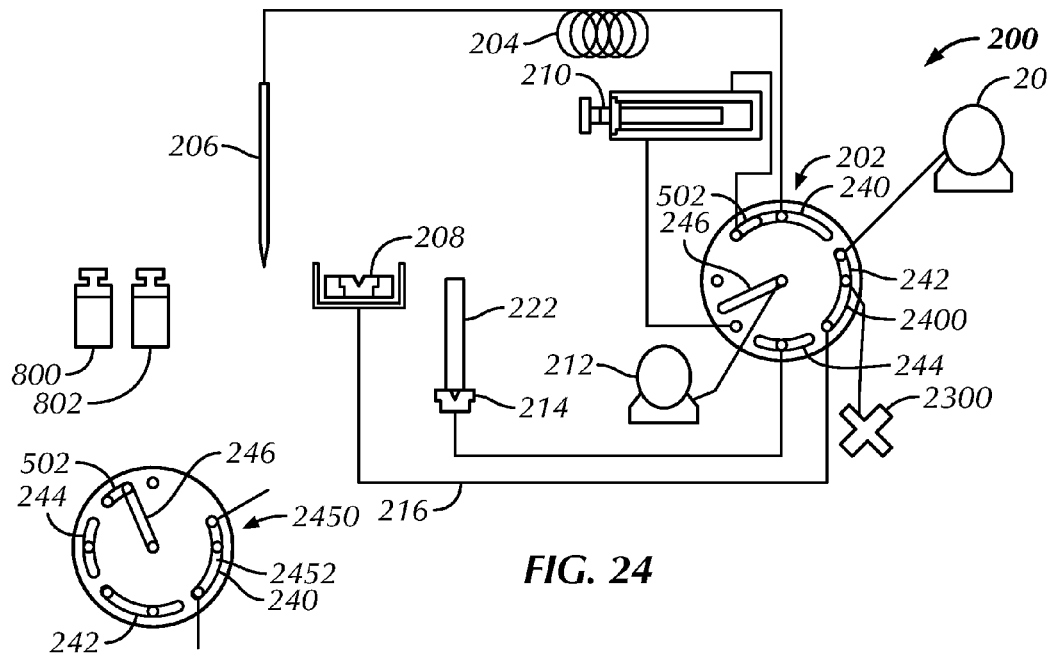
FIG. 24 shows the sample injector of FIG. 23 during a blockage test.

In FIG. 24, another blockage test is carried out. For this purpose, the seat 208 and the injection valve's 202 metering input groove 2452 and bypass groove 2400 are tested. In the shown embodiment, the mobile phase drive 20 pumps through valve 202, bypass groove 2400, seat capillary 216 and seat 208. Another image 2450 in FIG. 24 shows a test of metering input groove 2452.

Figure 25:
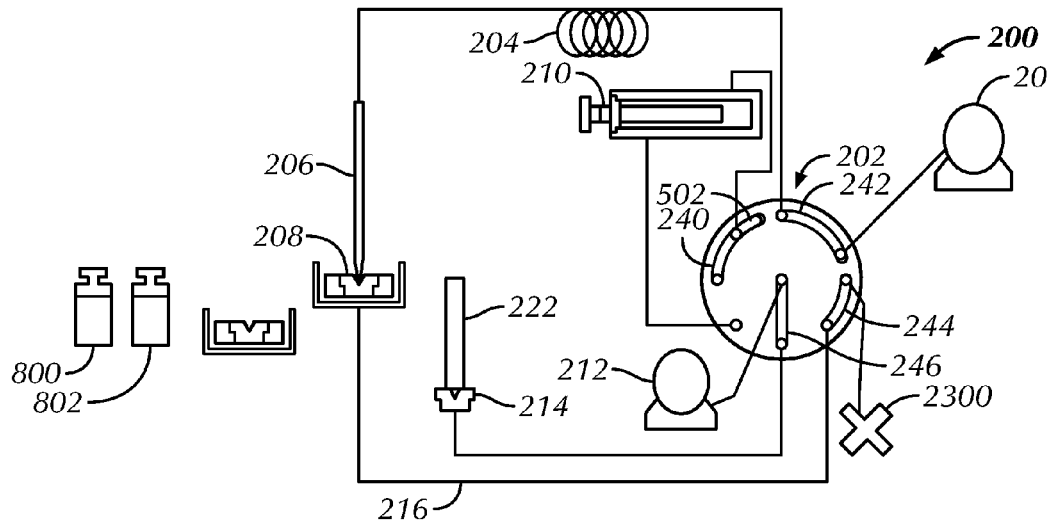
FIG. 25 shows the sample injector of FIG. 23 in an overall sampler and pump leak mode.

FIG. 25 shows another diagnostic operation mode in which an overall sampler and pump leak test is carried out. For this purpose, the analytical pump or mobile phase drive 20 is used which pumps a mobile phase through the valve 202, sample loop capillary 204, needle 206, seat 208, seat capillary 216 and again the valve 202.

Figure 26:
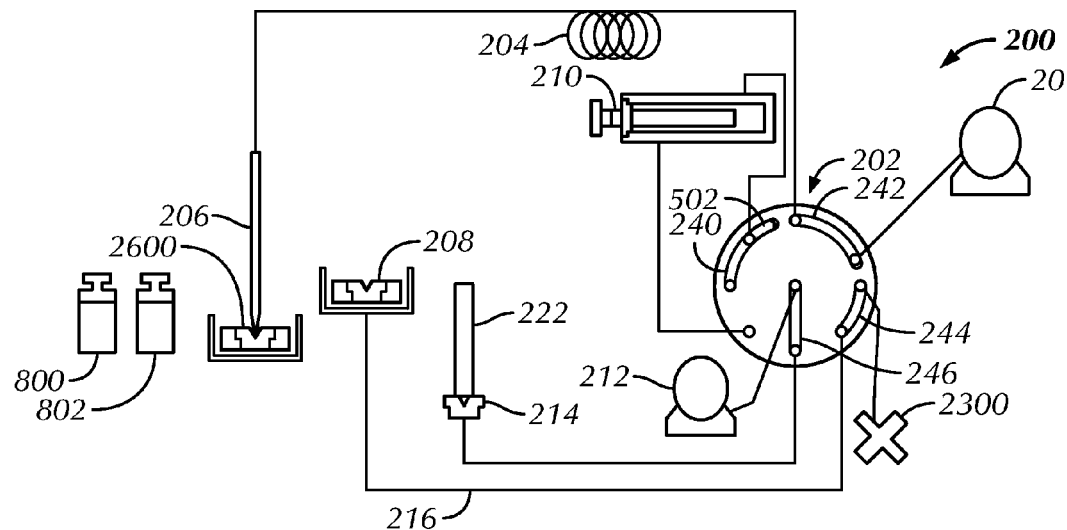
FIG. 26 shows the sample injector of FIG. 23 in a main pass leakage without seat mode.

FIG. 26 shows another diagnostic operation mode in which a main pass leakage without seat is tested. A blind seat 2600 is used for this purpose. Using the blind seat 2600, leakage of the loop capillary 204 including fittings can be tested. It can also be tested leakage of needle 206 including a fitting to the loop capillary 204. Cross-flow between injection valve's 202 inlet and outlet groove can also be tested (see also FIG. 27).

Figure 27:
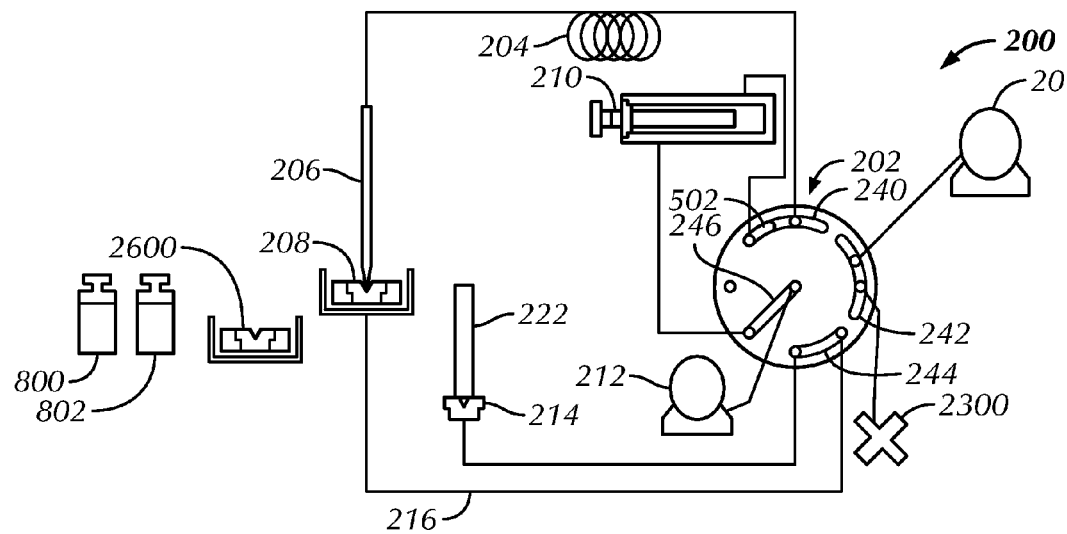
FIG. 27 shows the sample injector of FIG. 23 in a first leak bypass mode.

FIG. 27 shows a diagnostic feature by which a leak in a bypass can be tested. For this purpose, the analytical pump or mobile phase drive 20 is used. A cross-flow of bypass groove 242 to both the metering input groove 240 and the sample output groove 244 can be tested.

Figure 28:
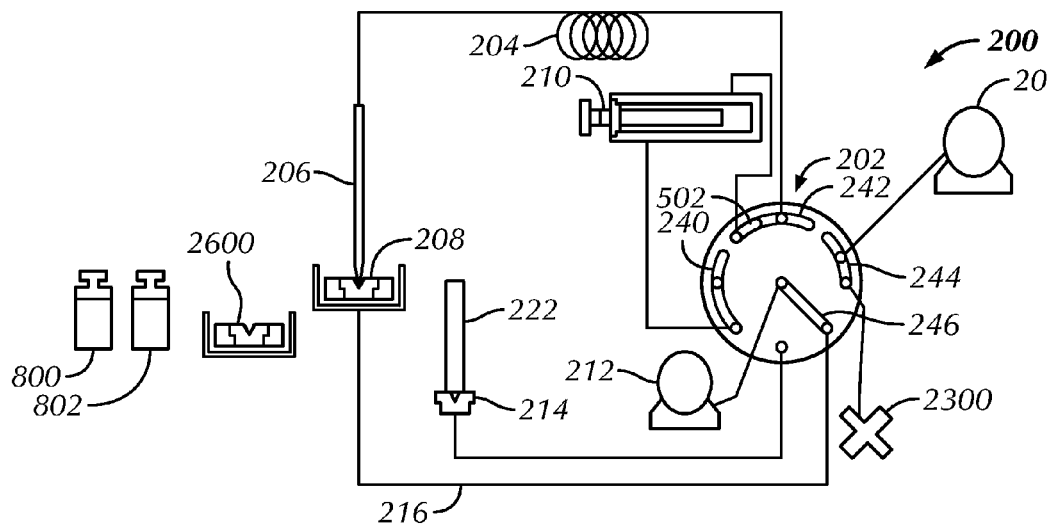
FIG. 28 shows the sample injector of FIG. 23 in a second leak bypass mode.

FIG. 28 shows a diagnostic feature according to another leak bypass mode. This relates to the standard injection operation mode discussed beforehand. FIG. 28 shows that the analytical pump or mobile phase drive 20 is used for this purpose.

Figure 29:
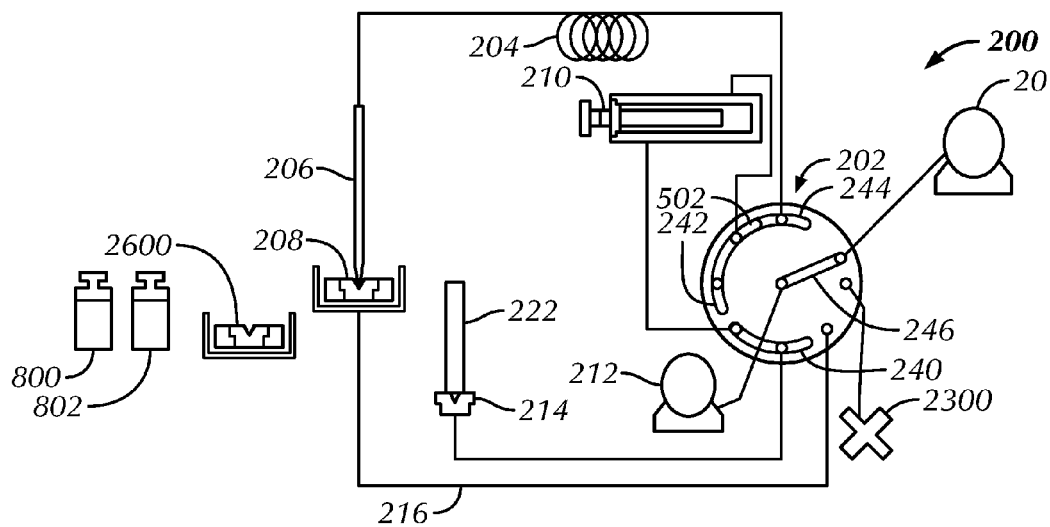
FIG. 29 shows the sample injector of FIG. 23 in a flush pump delivery test mode.

In FIG. 29, a flush pump delivery test for testing the functionality of the flush pump 212 is shown. For this purpose, it is possible to use a pressure sensor (not shown) which is part of the analytical pump or mobile phase drive 20. As can be taken from FIG. 29, a direct fluidic path is formed between flush pump 212, fluidic valve 202 and mobile phase drive 20.

Figure 30:
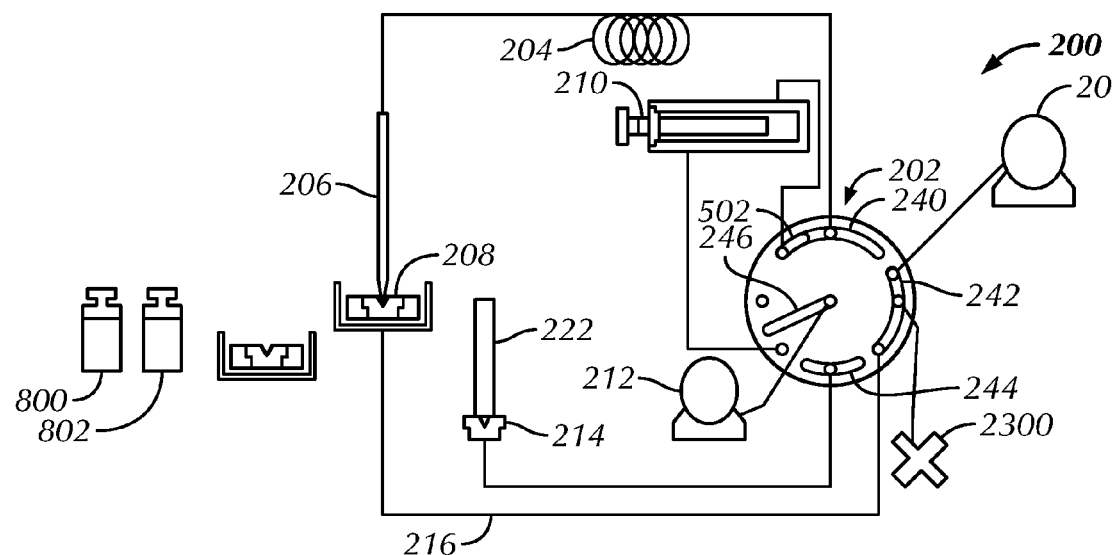
FIG. 30 shows the sample injector of FIG. 23 in a metering device leakage test mode.

FIG. 30 shows another diagnostic operation mode, in which leakage of the metering device 210 is tested. For this purpose, again the analytical pump or mobile phase drive 20 is used. A fluidic path from the mobile phase drive 20 via the fluidic valve 202, the seat capillary 216, the seat 208, the needle 206, the loop capillary 204, again the valve 202 and the metering pump 210 is shown.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A sample injector configured to introduce a sample fluid into a mobile phase, wherein the mobile phase is to be driven by a mobile phase drive through a separation unit for separating compounds of the sample fluid in the mobile phase, the sample injector comprising:
a sample loop for receiving the sample fluid,
a switchable valve for switching the sample loop between the mobile phase drive and the separation unit, wherein the switchable valve comprises;
a first valve member and a second valve member, wherein at least one of the first and second valve members is configured to be moved with respect to the other;
the first valve member comprises a plurality of ports;
the second valve member comprises a plurality of fluid paths for fluidly coupling respective ones of the ports in dependency on a relative movement position of the first and second valve members with respect to each other;
wherein the plurality of ports comprise eight circumferential ports distributed along a circumference of the first valve member and comprise one central port arranged at a central position of the first valve member;
wherein one of the circumferential ports has an extension groove; wherein the plurality of fluid paths comprise three arcuate fluid paths each being arcuate so as to be couplable with at least two of the circumferential ports;
wherein the plurality of fluid paths comprise one straight fluid path extending between the central position and a circumferential position so as to be couplable with the central port and with one of the circumferential ports.

2. A sample injector for use in a fluid separation system for separating compounds of a sample fluid in a mobile phase, the fluid separation system comprising a mobile phase drive to drive the mobile phase and comprising a separation unit for separating compounds of the sample fluid in the mobile phase, the sample injector comprising:
exactly one switchable valve;
a sample loop in fluid communication with a port of the valve and configured for receiving the sample fluid;
a needle in fluid communication with the sample loop;
a seat for receiving the needle;
a seat capillary in fluid communication with the seat and with a port of the valve;
wherein the valve is configured to be switchable no as to activate at least one selected of the following operation modes;
a) a bypass mode in which the valve fluidically couples the mobile phase drive with the separation unit via the valve;
b) a flush mode in which the valve enables flushing of at least one of the group consisting of the needle and the seat;
c) a block mode in which the valve fluidically couples at least the sample loop, the needle, the seat and the seat capillary to one another and fluidically decouples at least the sample loop, the needle, the seat and the seat capillary from the mobile phase drive and from ambient pressure.

3. The sample injector of claim 2, wherein the valve is configured to be switchable in a wash mode in which an exterior of the needle is washed.

4. The sample injector of claim 2, wherein the valve is configured to be switchable in a sample fluid intake mode in which the sample fluid is intaken into the sample loop via the needle by a metering device.

5. The sample injector of claim 2, wherein the valve is configured to be switchable in a diagnosis mode in which a selectable fluidic part of the fluid separation system is diagnosable, particularly with respect to at least one of the group consisting of blockage of the fluidic part and leakage in the fluidic part.

6. The sample injector of claim 2, wherein the valve is configured to be switchable in a sample fluid injection mode in which the sample fluid is injected into a fluidic channel between the mobile phase drive and the separation unit.

7. The sample injector of claim 2, comprising at least one of the following features:
the sample injector further comprises a metering device in fluid communication with two ports of the valve and configured for introducing a metered amount of the sample fluid on the sample loop, wherein the valve is configured to be switchable so that in the block mode the valve fluidically decouples also the metering device from the mobile phase drive and from ambient pressure;
the valve is configured to be switchable so that the valve enables back flushing of the seat in the flush mode;
the sample injector further comprises a flush pump, particularly exactly one flush pump, in fluid communication with a port of the valve and configured for flushing of at least one of the group consisting of the needle and the seat;
the sample injector further comprises a wash port in fluid communication with a port of the valve and configured for washing the needle, particularly for washing selectively an exterior surface of the needle or an interior surface of the needle;
the valve is configured according to claim 1.

8. A sample injector for use in a fluid separation system for separating compounds of a sample fluid in a mobile phase, the fluid separation system comprising a mobile phase drive to drive the mobile phase and comprising a separation unit for separating compounds of the sample fluid in the mobile phase, the sample injector comprising:
exactly one switchable valve;

a sample loop in fluid communication with a port of the valve and configured for receiving the sample fluid;
a needle in fluid communication with the sample loop;
a seat for receiving the needle;
a seat capillary in fluid communication with the seat and a port of the valve;
exactly one flush pump in fluid communication with a port of the valve and configured for flushing of at least one of the group consisting of the needle and the seat;
a wash port in fluid communication with a port of the valve;
wherein the valve is configured to be switchable so as to activate at least one selected of the following operation modes:
a) a sample path flush mode in which at least the sample loop, the needle, the seat and the seat capillary are flushed by the flush pump;
b) a seat back flush mode in which the seat is back flushed by the flush pump;
c) a needle wash mode in which the needle is washed in the wash port.

9. The sample injector of claim 8, wherein the needle wash mode comprises at least one of the group consisting of an external needle wash mode in which an external surface of the needle is washed in the wash port, and an internal needle wash mode in which an internal surface of the needle is washed in the wash port.

10. The sample injector of claim 8, wherein the valve is configured to be switchable so as to activate at least one selected of the following operation modes:
a) a bypass mode in which the valve fluidically couples the mobile phase drive with the separation unit via the valve;
b) a block mode in which the valve fluidically decouples at least the sample loop, the needle, the seat and the seat capillary from the mobile phase drive and ambient pressure;
c) a sample fluid intake mode in which the sample fluid is intaken into the sample loop via the needle driven by a metering device in fluid communication with two ports of the valve and configured for introducing a metered amount of the sample fluid on the sample loop;
d) a diagnosis mode in which a selectable fluidic part of the fluid separation system is diagnosable, particularly with respect to at least one of the group consisting of blockage of the fluidic part and leakage in the fluidic part;
e) a sample fluid injection mode in which the sample fluid is injected into a fluidic channel between the mobile phase drive and the separation unit.

11. The sample injector of claim 8,
wherein the switchable valve comprises;
a first valve member and a second valve member, wherein at least one of the first and second valve members is configured to be moved with respect to the other;
the first valve member comprises a plurality of ports;
the second valve member comprises a plurality of fluid paths for fluidly coupling respective ones of the ports in dependency on a relative movement position of the first and second valve members with respect to each other;
wherein the plurality of ports comprise eight circumferential ports distributed along a circumference of the first valve member and comprise one central port arranged at a central position of the first valve member;
wherein one of the circumferential ports has an extension groove; wherein the plurality of fluid paths comprise three arcuate fluid paths each being arcuate so as to be couplable with at least two of the circumferential ports;
wherein the plurality of fluid paths comprise one straight fluid path extending between the central position and a circumferential position so as to be couplable with the central port and with one of the circumferential ports.

* * * * *